(12) United States Patent
Kitaoka et al.

(10) Patent No.: US 11,382,651 B2
(45) Date of Patent: Jul. 12, 2022

(54) MEDICAL DEVICE AND TREATMENT METHOD

(71) Applicant: TERUMO KABUSHIKI KAISHA, Tokyo (JP)

(72) Inventors: Takashi Kitaoka, Hadano (JP); Masaomi Imai, Kofu (JP); Yuki Masubuchi, Hadano (JP); Takahiro Chida, Kanagawa (JP); Kazuaki Kanamoto, Hadano (JP); Hideki Fujimagari, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 195 days.

(21) Appl. No.: 16/274,611

(22) Filed: Feb. 13, 2019

(65) Prior Publication Data

US 2019/0175212 A1    Jun. 13, 2019

Related U.S. Application Data

(63) Continuation of application No. PCT/JP2017/029640, filed on Aug. 17, 2017.

(30) Foreign Application Priority Data

Aug. 23, 2016   (JP) .............................. JP2016-162423

(51) Int. Cl.
*A61B 17/3207* (2006.01)
*A61B 17/221* (2006.01)
(Continued)

(52) U.S. Cl.
CPC .... *A61B 17/320758* (2013.01); *A61B 17/221* (2013.01); *A61B 17/3207* (2013.01);
(Continued)

(58) Field of Classification Search
CPC ........... A61B 17/320758; A61B 2017/320766; A61B 17/320725; A61B 17/221; A61B 2017/2212
See application file for complete search history.

(56) References Cited

U.S. PATENT DOCUMENTS 5,336,234 A    8/1994  Vigil et al.
5,766,191 A    6/1998  Trerotola
(Continued)

FOREIGN PATENT DOCUMENTS

CN    103347453 A    10/2013
CN    104053410 A    9/2014
(Continued)

OTHER PUBLICATIONS

The extended European Search Report dated Jan. 3, 2020, by the European Patent Office in corresponding European Patent Application No. 17843497.3-1113. (9 pages).
(Continued)

*Primary Examiner* — Wade Miles
(74) *Attorney, Agent, or Firm* — Buchanan Ingersoll & Rooney PC

(57) ABSTRACT

A medical device and a treatment method are disclosed capable of breaking an object in a body lumen efficiently with a lower burden on body lumen tissues. A medical device is disclosed that is inserted into the body lumen so as to crush an object in the body lumen, the medical device including: an elongated shaft that is to be rotatably driven, and a deformable breaking member that is connected to the shaft so as to be rotatable and extends along the shaft. The breaking member has a first contact portion and a second contact portion. The first contact portion is located most outward in the radial direction of the breaking member in a state in which the breaking member is expanded radially outward. The second contact portion is located more out-
(Continued)

ward in the radial direction of the breaking member than the first contact portion in a contracted state.

24 Claims, 24 Drawing Sheets

(51) Int. Cl.
    *A61B 17/00*     (2006.01)
    *A61B 17/22*     (2006.01)

(52) U.S. Cl.
    CPC ............... *A61B 2017/00292* (2013.01); *A61B 2017/2212* (2013.01); *A61B 2017/22038* (2013.01); *A61B 2017/320741* (2013.01)

(56) References Cited

U.S. PATENT DOCUMENTS

| | | | |
|---|---|---|---|
| 5,836,868 A | | 11/1998 | Ressemann et al. |
| 2004/0133223 A1 | | 7/2004 | Weber |
| 2006/0058836 A1 | | 3/2006 | Bose et al. |
| 2014/0005712 A1 | * | 1/2014 | Martin ................ A61B 17/221 |
| | | | 606/200 |
| 2014/0005713 A1 | | 1/2014 | Bowman |
| 2014/0012283 A1 | | 1/2014 | Yasuda et al. |
| 2016/0120565 A1 | | 5/2016 | Kobayashi et al. |

FOREIGN PATENT DOCUMENTS

| | | |
|---|---|---|
| CN | 104619271 A | 5/2015 |
| EP | 0 820 729 A1 | 1/1998 |
| JP | H0767967 A | 3/1995 |
| JP | 2006512952 A | 4/2006 |
| JP | 2016087151 A | 5/2016 |
| WO | 2012141213 A1 | 10/2012 |
| WO | 2016/061373 A1 | 4/2016 |

OTHER PUBLICATIONS

International Search Report (PCT/ISA/210) dated Oct. 31, 2017, by the Japanese Patent Office as the International Searching Authority for International Application No. PCT/JP2017/029640.
Written Opinion (PCT/ISA/237) dated Oct. 31, 2017, by the Japanese Patent Office as the International Searching Authority for International Application No. PCT/JP2017/029640.
Office Action (Notification of the First Office Action) dated Dec. 22, 2020, by the National Intellectual Property Administration, PRC in corresponding Chinese Patent Application No. 201780051865.2 and an English Translation of the Office Action. (17 pages).

* cited by examiner

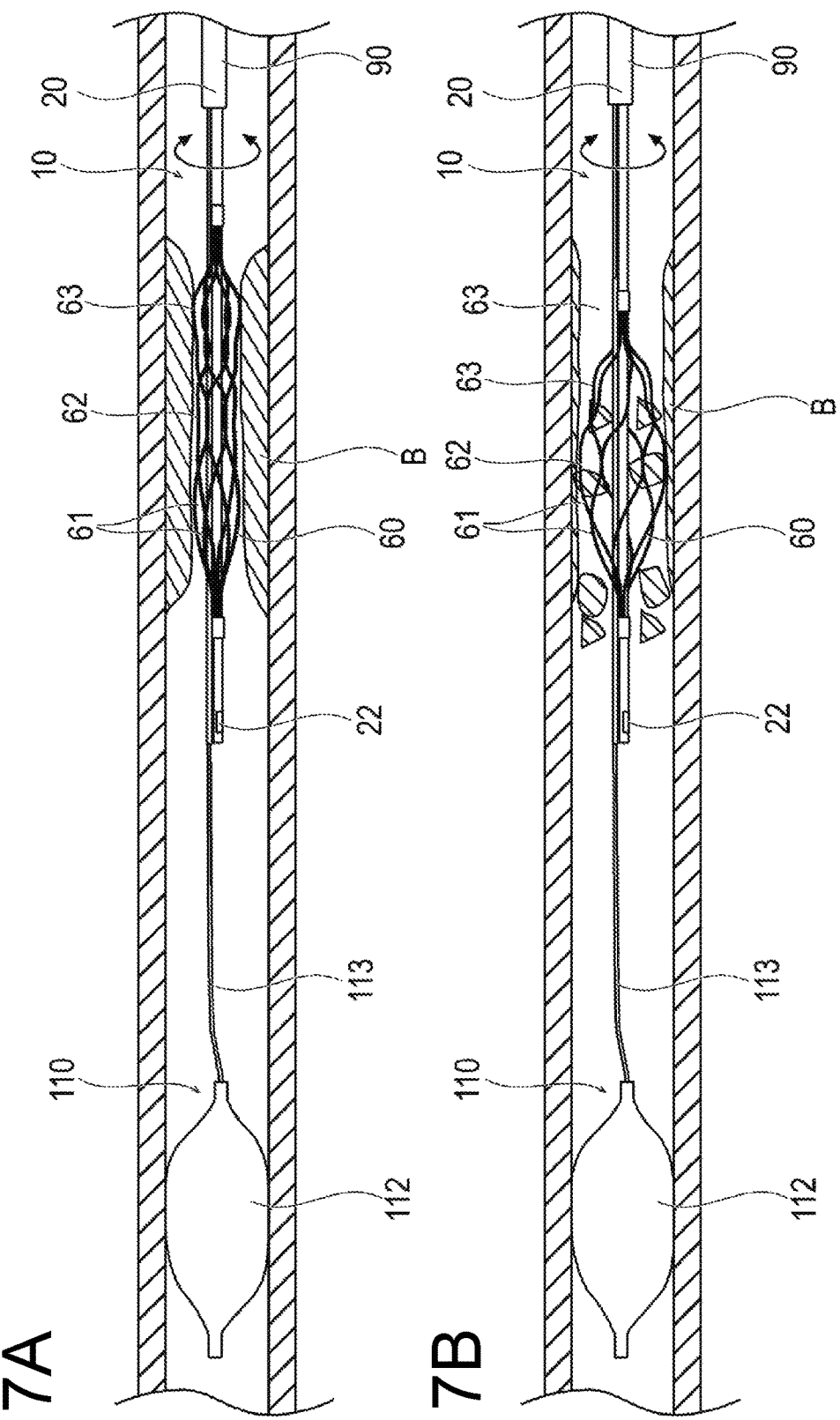

MEDICAL DEVICE AND TREATMENT METHOD

CROSS-REFERENCES TO RELATED APPLICATIONS

This application is a continuation of International Application No. PCT/JP2017/029640 filed on Aug. 18, 2017, which claims priority to Japanese Application No. 2016-162423 filed on Aug. 23, 2016, the entire content of both of which is incorporated herein by reference.

FIELD OF THE DISCLOSURE

The present disclosure generally relates to a medical device and a treatment method using the medical device that is used for breaking an object in a body lumen.

BACKGROUND DISCUSSION

In a case where a thrombus occurs in a body lumen, it is necessary to promptly remove the thrombus. An example of a symptom of the thrombus that occurs in the body lumen can include a deep vein thrombosis due to a thrombus that occurs in a vein such as a femoral vein or a popliteal vein in a relatively deep portion of a body. As a medical treatment method of the deep vein thrombosis, there is a known method of removing a thrombus by inserting an elongated tubular body of a medical device into a blood vessel, injecting a medicine such as a thrombolytic agent in an embolus, and dissolving the thrombus.

A medical treatment method of injecting a medicine in order to remove the thrombus entails a side effect such as bleeding. A medical treatment method is proposed in which a member of a wire that is provided at a distal portion of a shaft inserted into a blood vessel is rotated, and thereby an embolus (for example, a thrombus) with which the member comes into contact is mechanically broken such that a patency rate (i.e., rate of a region that is not blocked to a cross section of the blood vessel) increases (for example, refer to U.S. Pat. No. 5,766,191). Consequently, medicine or medicine usage can be eliminated or reduced.

The performance (i.e., breaking ability) of a device, which breaks the embolus in a lumen structure of the blood vessel through rotation so as to increase the patency rate, depends on a parameter such as a rotation speed of a rotating body, radially outward pressure, or a shape of an outermost surface (portion that comes into contact with the embolus) of the rotating body.

When the breaking ability of the embolus improves, a load on lumen tissue can also increase. Therefore, there is a demand for a rotating body that is capable of breaking the embolus efficiently while the load to the lumen tissue is suppressed.

SUMMARY

A medical device is disclosed, which is capable of breaking an object in body lumen efficiently with a lower burden on body lumen tissues and to provide a treatment method using such a medical device.

A medical device is disclosed that is to be inserted into a body lumen so as to break an object in the body lumen, the medical device including: an elongated shaft that is rotatably driven; and a deformable breaking member that is connected to the shaft so as to be rotatable and extends along the shaft. The breaking member has a first contact portion and a second contact portion. The first contact portion is located on the outermost side of the breaking member in a radial direction of the breaking member in a state in which the breaking member is expanded toward the outer side in the radial direction. The second contact portion in a contracted state rather than the expanded state is located more outward in the radial direction of the breaking member than the first contact portion.

A treatment method is disclosed for breaking an object in a body lumen by using the medical device described above, the treatment method including: a step of inserting the shaft into the body lumen and delivering the breaking member to the vicinity of the object; and a step of inserting the breaking member into a gap of the object and rotating the breaking member by the shaft to break the object while deforming the breaking member due to own elastic force depending on a size of the gap of the object to change a contact position with the object to the first contact portion or the second contact portion in a radial direction.

According to the medical device and the treatment method configured as described above, in a case where a small amount of the object is present in the body lumen and a patency rate is high, the breaking member comes into an expanded state so that the first contact portion is located most outward, which makes it possible to reduce the burden on lumen tissues. In a case where a large amount of the object is present in the body lumen and the patency rate is low, the breaking member is contracted so that the second contact portion is located more outward than the first contact portion, which makes it possible to break the object in the body lumen relatively efficiently.

A medical device is disclosed configured to be inserted into a body lumen to break an object in the body lumen, the medical device comprising: an elongated shaft that is rotatably driven; and a deformable breaking member that is connected to the shaft and configured to be rotatable and extends along the shaft, the breaking member having a first contact portion and a second contact portion, the first contact portion being located more outward in a radial direction of the breaking member than the second contact portion in a state in which the breaking member is expanded radially outward, and wherein the second contact portion is located more outward in the radial direction of the breaking member than the first contact portion in a contracted state.

A medical device is disclosed configured to be inserted into a body lumen to break an object in the body lumen, the medical device comprising: an elongated shaft that is rotatably driven; and deformable breaking members that are connected to the elongated shaft and configured to be rotatable, the deformable members extending along the shaft and arranged along a circumferential direction, wherein the breaking members have a first contact portion and a second contact portion, the second contact portion being more rigid than the first contact portion.

A treatment method is disclosed for breaking an object in a body lumen by using the medical device, the treatment method comprising: inserting a medical device into the body lumen in a contracted state, the medical device including an elongated shaft configured to be rotatably driven, and a deformable fragmenting part that is connected to the shaft and configured to be rotatable and extends along the shaft, the deformable fragmenting part having a first contact portion and a second contact portion, the second contact portion being located more outward in a radial direction of the deformable fragmenting part than the first contact portion in the contracted state; inserting the deformable fragmenting part into a gap of the object; and rotating the deformable fragmenting part by the shaft to break the object with the second contact portion

BRIEF DESCRIPTION OF THE DRAWINGS

FIGS. 4A and 4B illustrate side views of the breaking member of the medical device, wherein FIG. 4A illustrates an expanded state, and FIG. 4B illustrates a contracted state.

FIGS. 5A and 5B illustrate front views of the breaking member of the medical device when viewed from a distal side, wherein FIG. 5A illustrates the expanded state, and FIG. 5B illustrates the contracted state.

FIGS. 6A and 6B illustrate cross-sectional views of states in a blood vessel, wherein FIG. 6A illustrates a state in which the medical device is inserted into the blood vessel, and FIG. 6B illustrates a state in which the breaking member of the medical device is exposed in the blood vessel.

FIGS. 7A and 7B illustrate cross-sectional views of states in the blood vessel, wherein FIG. 7A illustrates a state in which the breaking member in the contracted state breaks a thrombus, and FIG. 7B illustrates a state in which the breaking member in the expanded state breaks the thrombus.

FIGS. 8A-8D illustrate cross-sectional views of the breaking member that rotates in the thrombus, wherein FIG. 8A illustrates a state in which the breaking member rotates, FIG. 8B illustrates a state in which the breaking member stops, FIG. 8C illustrates a state in which the breaking member rotates in a reverse direction, and FIG. 8D illustrates a state in which the breaking member stops again.

FIGS. 9A and 9B illustrate cross-sectional views of the breaking member that rotates in the thrombus, wherein FIG. 9A illustrates a state in which the breaking member rotates in a projection direction of a second curved portion, and FIG. 9B illustrates a state in which the breaking member is expanded.

FIGS. 10A and 10B illustrate cross-sectional views of the breaking member that rotates in the thrombus, wherein FIG. 10A illustrates a state in which the breaking member rotates in a reverse direction of the projection direction of the second curved portion, and FIG. 10B illustrates a state in which the breaking member is contracted.

FIGS. 14A and 14B illustrate side views of the breaking member of the medical device according to the second embodiment, wherein FIG. 14A illustrates an expanded state, and FIG. 14B illustrates a contracted state.

FIGS. 15A and 15B illustrate front views of the breaking member of the medical device according to the second embodiment when viewed from a distal side, wherein FIG. 15A illustrates an expanded state, and FIG. 15B illustrates a contracted state.

FIGS. 18A and 18B illustrate side views of the breaking member of the medical device according to the third embodiment, wherein FIG. 18A illustrates an expanded state, and FIG. 18B illustrates a contracted state.

FIGS. 19A and 19B illustrate front views of the breaking member of the medical device according to the third embodiment when viewed from a distal side, wherein FIG. 19A illustrates an expanded state, and FIG. 19B illustrates a contracted state.

FIGS. 20A and 20B illustrate side views of the breaking member of the medical device according to a fourth embodiment, wherein FIG. 20A illustrates an expanded state, and FIG. 20B illustrates a contracted state.

DETAILED DESCRIPTION

Figure 1:
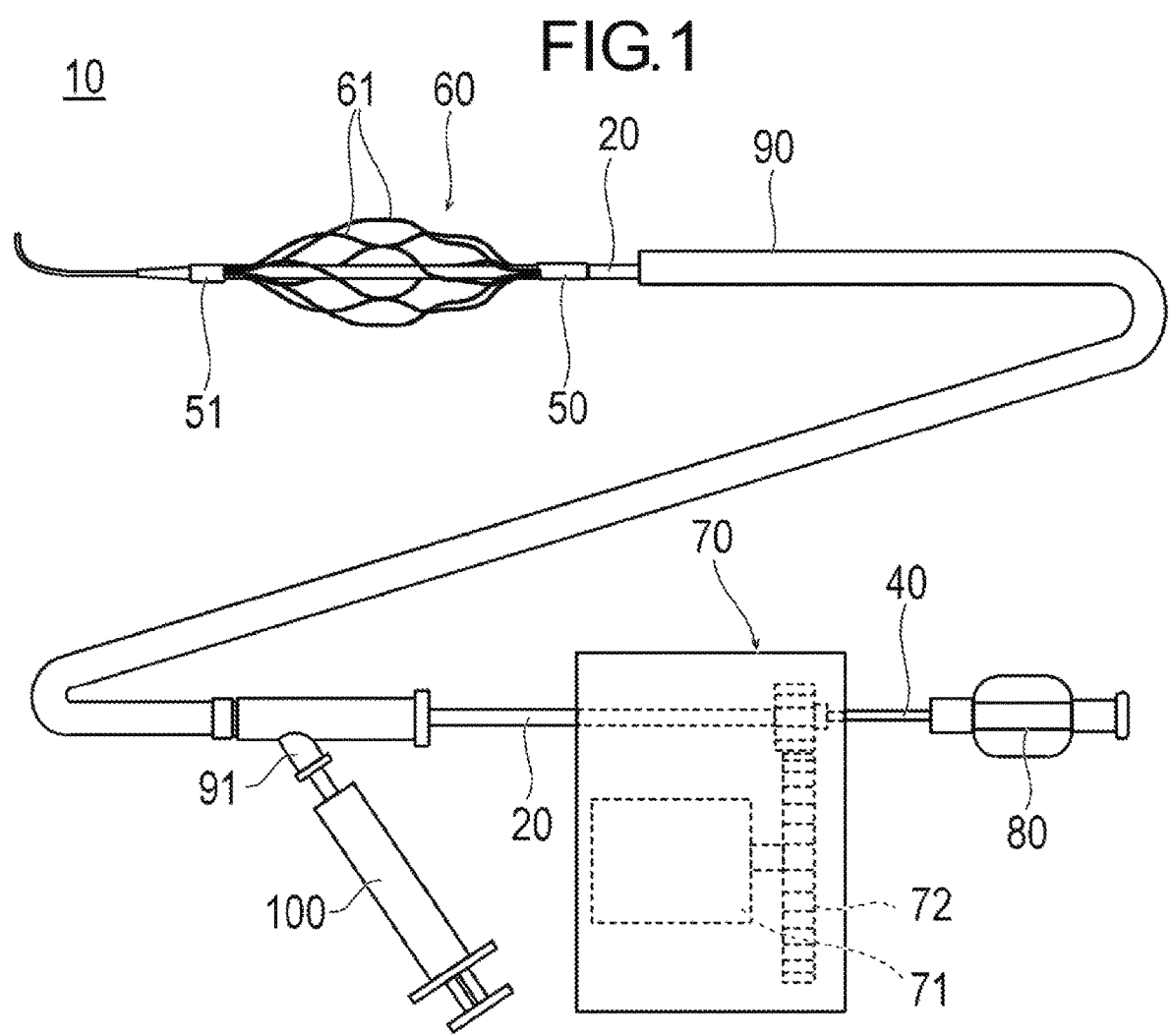
FIG. 1 is a plan view illustrating a medical device according to a first embodiment.

Hereinafter, embodiments of the disclosure will be described with reference to the drawings. Incidentally, a dimension ratio in the drawings is enlarged depending on the description and the ratio is different from an actual ratio in some cases.

First Embodiment

A medical device 10 according to a first embodiment is inserted into a blood vessel and is used for a procedure of breaking and removing a thrombus in a deep-vein thrombosis. In this disclosure, a side of the device, which is inserted into a blood vessel, is referred to as a "distal side", and a hand side, on which an operation is performed, is referred to as a "proximal side". Incidentally, an object to be removed is not necessarily limited to the thrombus but can correspond to any object that can be present in a body lumen.

In accordance with an exemplary embodiment, as illustrated in FIG. 1, the medical device 10 includes a shaft 20 that is elongated and is rotatably driven, an outer sheath 90 that can accommodate the shaft 20, a sliding portion 50 that is capable of sliding with respect to the shaft 20, and a breaking member (or fragmenting part) 60 that is rotated by the shaft 20. The medical device 10 further includes a rotation-driving portion 70 that rotates the shaft 20, a guide wire housing 40 into which a guide wire can be inserted, a hub 80 that is provided at a proximal-side end portion of the guide wire housing 40, and a syringe 100 that is connected to side tube 91 on the proximal side of the outer sheath 90.

A proximal-side end portion of the shaft 20 is located in the rotation-driving portion 70. The shaft 20 is capable of reciprocating in a circumferential direction by the rotation-driving portion 70. However, the shaft 20 is not limited to a portion that reciprocates and may be a portion that rotates in one direction.

The guide wire housing 40 is provided in a range from a distal-side end portion to the hub 80 inside a hollow of the shaft 20. The guide wire housing 40 has a guide wire lumen into which a guide wire is insertable.

The outer sheath 90 is disposed to be coaxial with the shaft 20 on an outer side of the shaft 20. In accordance with an exemplary embodiment, a lumen of the outer sheath 90 not only houses the breaking member (i.e., deformable fragmenting part or deformable fragmenting member) 60 but also functions as an aspiration lumen that comes into a negative pressure state and generates an aspirating force. In accordance with an exemplary embodiment, a proximal-side end portion of the outer sheath 90 diverges into a Y shape, and the shaft 20 extends to the rotation-driving portion 70 in one of divergence portions. The syringe 100 can be connected to the side tube 91, the side tube 91 being another one of divergence portions. The syringe 100 is connected to side tube 91, thereby, performing aspiration in the lumen of the outer sheath 90, and thus a pressure in the lumen can come into a negative pressure state. In addition, the syringe 100 is connected to the side tube 91, and thereby it is possible to inject a thrombolytic agent into the lumen of the outer sheath 90 from the syringe 100.

In accordance with an exemplary embodiment, the breaking member 60 is provided at a distal portion of the shaft 20. The breaking member 60 has a plurality of (for example, in the embodiment, six) wires 61. Each of the wires 61 curves in a three-dimensional manner. Incidentally, the number of wires 61 is not particularly limited. In accordance with an exemplary embodiment, the wires 61 are all twisted in the same circumferential direction along an axial direction of the shaft 20. Proximal-side end portions of the wires 61 are each fixed to the sliding portion 50 that is slidable with respect to the shaft 20. Distal-side end portions of the wires 61 are each fixed to a fixing portion 51 that is fixed to the shaft 20. Fixing positions of the wires 61 to the fixing portion 51 and the sliding portion 50 are arranged in the circumferential direction. Substantial center portions of the wires 61 in the axial direction in which the wires curve are arranged in the circumferential direction at a position that is separated from the shaft 20 in the radial direction. Consequently, the entire breaking member 60 is uniformly expanded in the circumferential direction. When the shaft 20 rotates, the breaking member 60 rotates along with the shaft. Therefore, it is possible to break a thrombus in a blood vessel or agitate the broken thrombus. In accordance with an exemplary embodiment, the breaking member is not only the wire but also may be a laser-cut pipe, for example, a stent.

Figure 2:
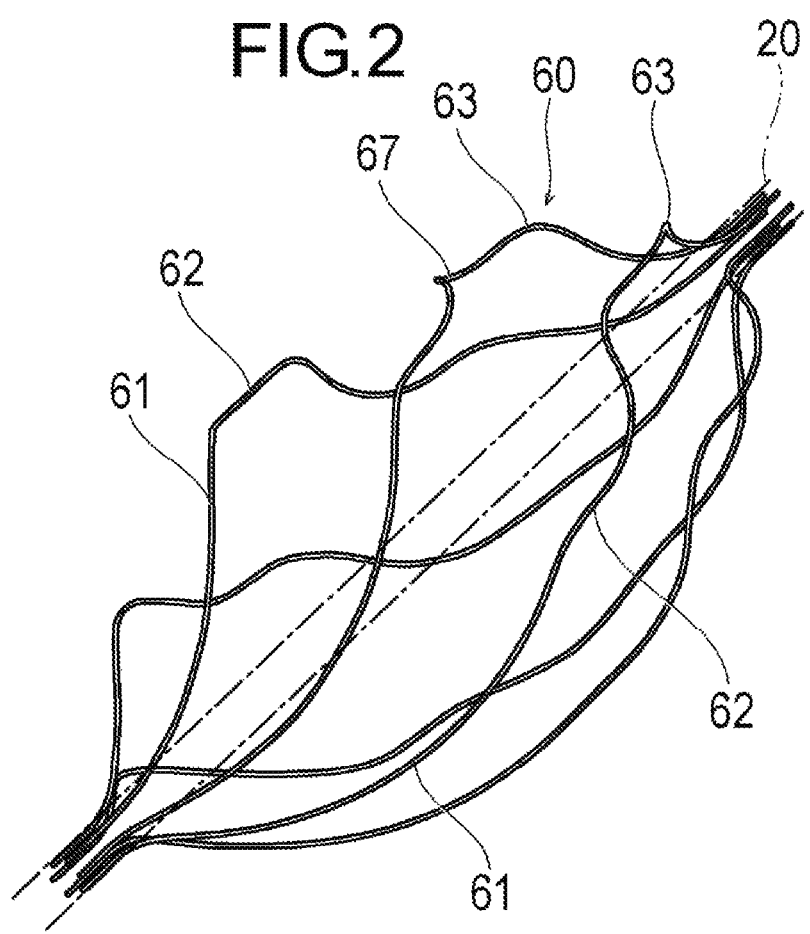
FIG. 2 is a perspective view illustrating a breaking member (or fragmenting part) of the medical device.
Figure 4A:
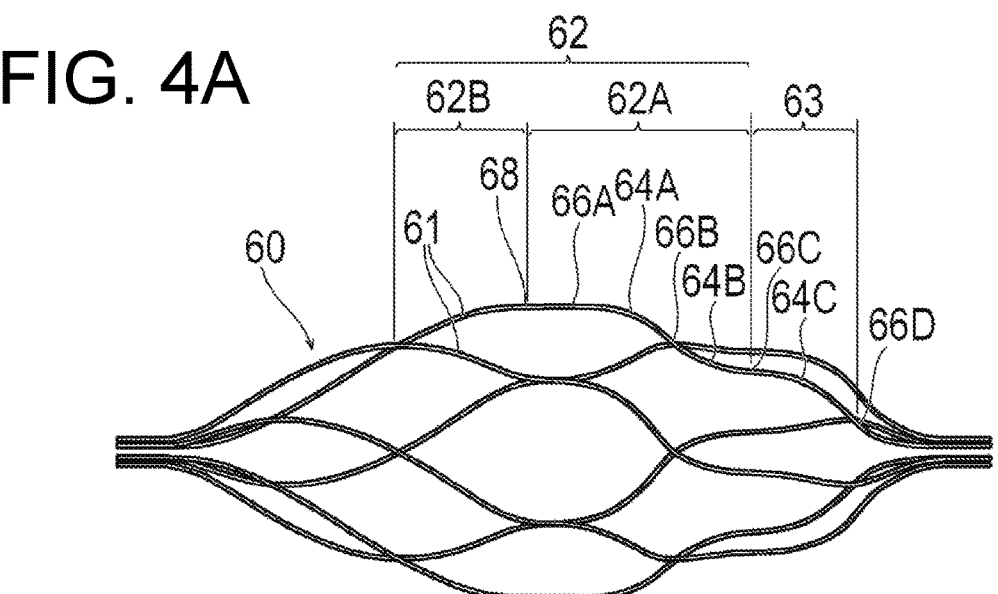
Figure 5A:
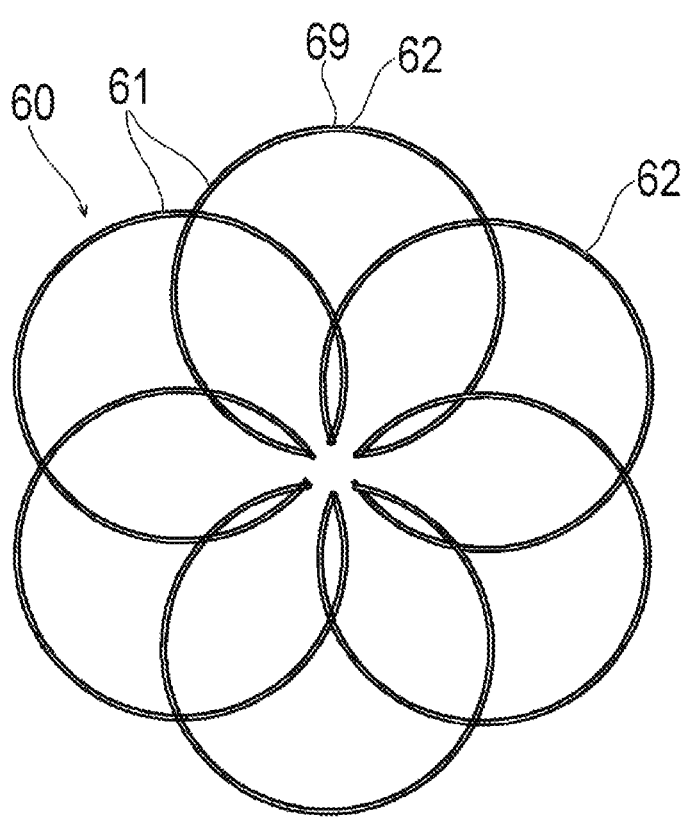

In accordance with an exemplary embodiment, the breaking member 60 is expanded radially outward and comes into a natural state in which no external force acts on the breaking member 60. The natural state means a state in which no external force is applied to the breaking member 60 and a state in which the breaking member 60 is located outside of the outer sheath 90 or outside of a blood vessel having a diameter larger than that of the breaking member 60. An expanded state means a state in which a first contact portion 62 of the breaking member 60 is located more on an outer side in the radial direction of the breaking member 60 than a second contact portion 63. The natural state is included as a part of the expanded state and is a state in which no external force is applied to the breaking member 60. As illustrated in three-dimensional views of FIGS. 2, 4A, and 5A, in the natural state, the breaking member 60 has the first contact portion 62 on the outermost side in the radial direction of the breaking member 60. That is, the first contact portion 62 is located in a part of the breaking member 60 having the largest outer diameter in the axial direction. In FIGS. 2, 4A, and 5A, the first contact portion 62 is located at the substantially center portion of the breaking member 60 in the axial direction. In the expanded state, the first contact portion 62 is a part located more radially outward than the second contact portion 63 of the breaking member 60 to be described below. A shape of each of the wires 61 in the expanded state is substantially identical with a shape of each of the wires 61 in the natural state in which no external force acts on each of the wires 61. In other words, the wires 61 are formed into a shape in the expanded state through a heat treatment in advance. Incidentally, the wires 61 may not need to be formed into the shape in the expanded state in advance.

Figure 3:
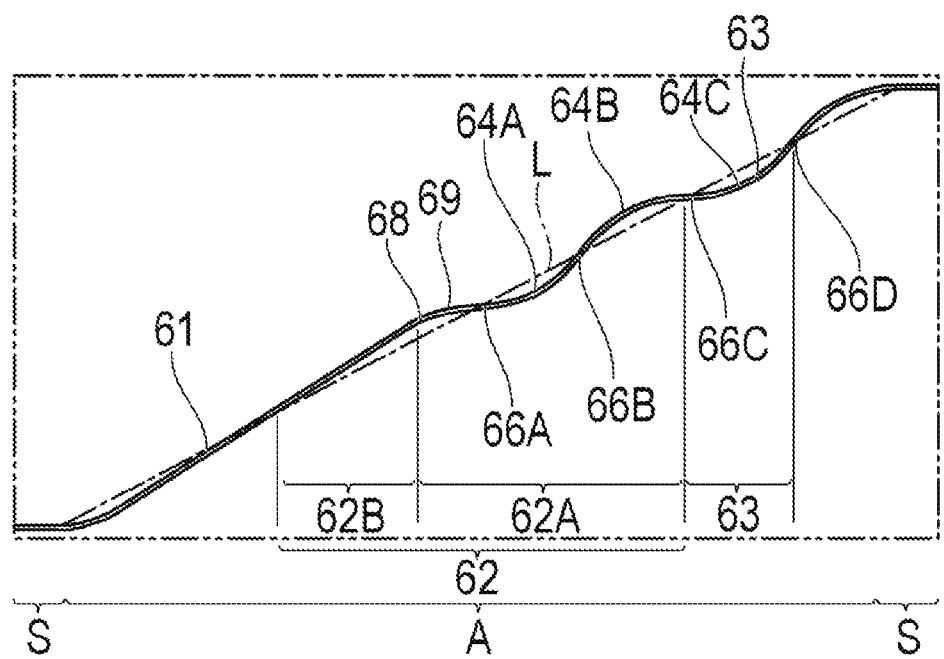
FIG. 3 is a developed view in a circumferential direction of a wire that configures the breaking member of the medical device.

In addition, as illustrated in FIG. 3, in a developed view in the circumferential direction in the expanded state, each of the wires 61 has a first convex portion 64A, a second convex portion 64B, and a third convex portion 64C on the proximal side in a range A excluding a fixing range S for fixing to the sliding portion 50 or the fixing portion 51. The first convex portion 64A, the second convex portion 64B, and the third convex portion 64C have equal curvature radius in the developed view in the circumferential direction. The first convex portion 64A and the third convex portion 64C project on the same side in the circumferential direction. In accordance with an exemplary embodiment, the first convex portion 64A and the third convex portion 64C projects, for example, by about 1.5 mm in a three-dimensional manner from a reference line L (a position of the wire in a case where the wire does not have the convex portions) represented by a dot-and-dash line in FIG. 3. The second convex portion 64B projects on an opposite side in the circumferential direction with respect to the first convex portion 64A and the third convex portion 64C. The second convex portion 64B projects, for example, by about 1.5 mm from the reference line L in a three-dimensional manner. Each of the wires 61 has a first inflection point 66A on the distal side of the first convex portion 64A and a second inflection point 66B between the first convex portion 64A and the second convex portion 64B. Each of the wires 61 has a third inflection point 66C between the second convex portion 64B and the third convex portion 64C. Each of the wires 61 has a fourth inflection point 66D on the proximal side of the third convex portion 64C. In accordance with an exemplary embodiment, each of the wires 61 may have more inflection points than three inflection points as shown in FIG. 3. In addition, each of the wires 61 has a transition portion 68 in which a straight line and a curve intersect each other in the developed view in the circumferential direction (two-dimension), more on the distal side than the first inflection point 66A. Each of the wires 61 has a vertex 69, at which largest outer diameter increases in the expanded state, in a range from the first convex portion 64A to the transition portion 68. A distance from a center axis of the shaft 20 to the wire 61, that is, a radius of the breaking member 60, is constant in a predetermined range including the vertex 69 in the axial direction or is approximately more constant, compared with a breaking member in a case where the wire does not have a convex portion. Consequently, in the expanded state, a wider range of the wires 61 in the axial direction can come into uniform contact with a contact target.

As shown in FIG. 3, the first contact portion 62 in the expanded state is located more radially outward than the second contact portion 63 and includes a curve and a straight line in the developed view in the circumferential direction. The first contact portion 62 has a third contact portion 62A having a curve shape and a fourth contact portion 62B having a straight line shape in the developed view in the circumferential direction. The third contact portion 62A is a range from the transition portion 68 to the third inflection point 66C. Hence, the third contact portion 62A has a first convex portion 64A and a second convex portion 64B. The fourth contact portion 62B is located more on the distal side than the transition portion 68 and is a part that is located more radially outward than the second contact portion 63. The second contact portion 63 is a range from the third inflection point 66C to the fourth inflection point 66D. Hence, the second contact portion 63 has the third convex portion 64C. The transition portion 68 is separated from the reference line L toward the same side as the side on which the second convex portion 64B projects, in the developed view in the circumferential direction. Incidentally, in the developed view in the circumferential direction, the first contact portion may have only a curve or may have only a straight line.

In the expanded state, the third contact portion 62A and the fourth contact portion 62B are located more radially outward than the second contact portion 63. In accordance with an exemplary embodiment, diameters of the third contact portion 62A and the fourth contact portion 62B are different from each other in some parts and are equal to each other in some parts. The outermost vertex 69 in the radial direction is located in the third contact portion 62A.

In accordance with an exemplary embodiment, portions of the wire 61 can have different hardness from each other with respect to contact targets in a condition of a shape or a position. In the expanded state, the second contact portion 63 that is close to an end portion of the breaking member 60 and has a curve is harder than the third contact portion 62A having a curve. The third contact portion 62A having the curve is harder than the fourth contact portion 62B having a curve and a straight line.

Figure 4B:
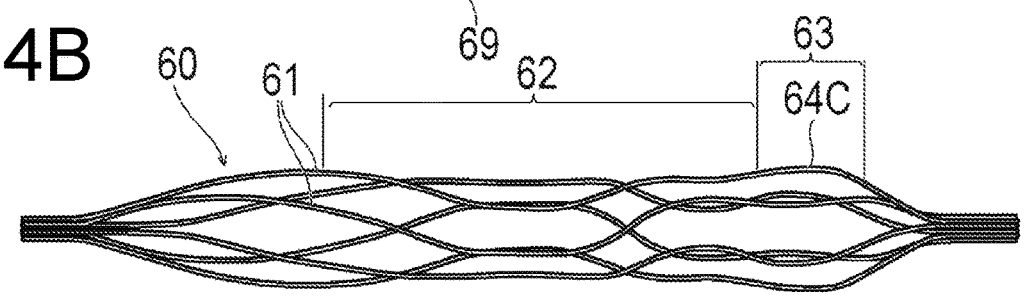
Figure 5B:
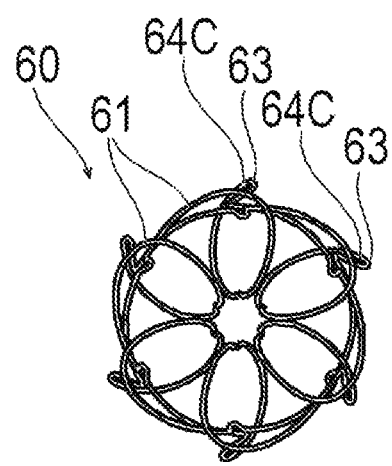

In a state (contracted state) in which the breaking member 60 is more contracted radially inward from the expanded state, each of the wires 61 has the second contact portion 63 on the outermost side in the radial direction, as illustrated in FIGS. 4B and 5B. The contracted state means a state in which the breaking member 60 is located inside a blood vessel having a diameter smaller than the outer sheath 90 and the breaking member 60 or a blood vessel that is clogged with a thrombus and has a diameter smaller than the breaking member 60 such that the second contact portion 63 is located on the outermost side in the radial direction. The second contact portion 63 is configured of the third convex portion 64C (refer to FIG. 3). In the contracted state, the first contact portion 62 is contracted to be smaller than the second contact portion 63 in the radial direction. In accordance with an exemplary embodiment, when the first contact portion 62 is located closer to the center portion of the breaking member 60 in the axial direction than the second contact portion 63, and thus the breaking member 60 is stretched in the axial direction, thereby, being contracted in the radial direction, the first contact portion approaches an outer surface of the shaft 20 more than the second contact portion 63. Further, the end portion of the breaking member 60 is fixed to the sliding portion 50 such that it is not possible to change a position and an orientation of the end portion, and thereby the second contact portion 63 that is closer to the end portion than the first contact portion 62 is influenced by the end portion such that the second contact portion is unlikely to be deformed and is unlikely to approach the outer surface of the shaft 20. Therefore, even when the breaking member 60 is stretched in the axial direction, thereby, being contracted in the radial direction, it can be difficult for the second contact portion 63 to approach the shaft 20, and thus the second contact portion 63 is located more outward in the radial direction than the first contact portion 62. Hence, in the expanded state, the first contact portion 62 is located more radially outward than the second contact portion 63. However, in the contracted state, the first contact portion 62 is located more radially inward than the second contact portion 63.

In accordance with an exemplary embodiment, the second contact portion 63 has a curvature radius smaller than that of the fourth contact portion 62B included in the first contact portion 62. Therefore, the first contact portion 62 and the second contact portion 63 can have different actions from each other on the contact target. In the embodiment, in the contracted state, when viewed from the distal side, the third convex portion 64C located in the second contact portion 63 has an outer diameter that is larger than the outer diameter of the first contact portion 62, and thereby the second contact portion 63 comes into contact with the thrombus or the lumen tissue. Incidentally, the second contact portion 63 curves in a three-dimensional manner, and thus the shape of the second contact portion changes depending on a direction of view. In the contracted state, when viewed from the front surface (distal side), the second contact portion 63 is observed as a steep projecting portion having a small width so as to overlap the wire 61 in the axial direction (refer to FIG. 5B). In addition, in the contracted state, when viewed from side, the second contact portion 63 is observed as a gentle projecting portion having a larger width, compared with the case of being viewed from the front surface (refer to FIG. 4B). In the expanded state, the fourth contact portion 62B included in the first contact portion 62 comes into contact with the thrombus or the lumen tissue in a shape approximate to a straight line. In addition, in the expanded state, the outer diameter of the first contact portion 62 is constant or approximately constant in a predetermined range including the vertex 69 in the axial direction. Therefore, the first contact portion 62 in the expanded state comes into smooth contact with the thrombus or the lumen tissue more than the second contact portion 63 in the contracted state.

In a three dimensional view, the second contact portion 63 has the same curvature radius as that of the first contact portion 62; however, it is possible to generate different actions from each other with respect to the contact target. In this case, the end portion of the breaking member 60 is fixed to the sliding portion 50 such that it is not possible to change a position and an orientation of the end portion, and thereby the second contact portion 63 that is closer to the end portion than the first contact portion 62 is influenced by the end portion such that the second contact portion is unlikely to be deformed and is unlikely to approach the outer surface of the shaft 20. In the contracted state, the second contact portion 63 is located more radially outward than the first contact portion 62. When viewed from the front surface (distal side), the third convex portion 64C located in the second contact portion 63 has an outer diameter that is larger than the outer diameter of the first contact portion 62, and thereby the second contact portion comes into contact with the thrombus or the lumen tissue. In addition, in the expanded state, the outer diameter of the first contact portion 62 is larger than the outer diameter of the second contact portion 63, unlike in the contracted state. In the expanded state, the first contact portion 62 is separated from the end portion of the breaking member 60, of which the position and the orientation is unlikely to be changed, and thus the first contact portion 62 comes into smooth contact with the thrombus or the lumen tissue more than the second contact portion 63 in the contracted state.

In the three dimensional view, the second contact portion 63 has a curvature radius smaller than that of the first contact portion 62 (fourth contact portion 62B), and thus the second contact portion 63 has a structure in which it is more difficult to be deformed against an applied force than the first contact portion 62. Hence, the second contact portion 63 has a relatively more rigid structure than that of the first contact portion 62 and has a relatively high breaking force and agitating force with respect to the contact target. In addition, in the three dimensional view, the second contact portion 63 may have the same curvature radius as that of the first contact portion 62. In this case, the end portion of the breaking member 60 is fixed to the sliding portion 50 such that it is not possible to change a position and an orientation of the end portion of the breaking member 60, and thereby the second contact portion 63 that is closer to the end portion than the first contact portion 62 is influenced by the end portion such that the second contact portion is unlikely to be deformed and is unlikely to approach the outer surface of the shaft 20. Hence, the second contact portion 63 has a relatively more rigid structure than that of the first contact portion 62 and has a relatively high breaking force and agitating force with respect to the contact target.

In addition, in the contracted state, the third convex portion 64C located in the second contact portion 63 has a radially outward convex shape when viewed from the front surface, and the second contact portion 63 has the convex shape that curves. Therefore, the second contact portion 63 easily enters (or breaks) into an object in the body lumen in the contracted state. In addition, in the contracted state, the second contact portion 63 has a convex shape toward the circumferential direction (rotating direction) of the breaking member 60, and the convex shape curves. Therefore, the second contact portion 63 rotates, thereby, easily entering (or breaking) into an object in the body lumen.

The wire 61 of the breaking member 60 can be made of a thin metal wire having flexibility. In accordance with an exemplary embodiment, the breaking member 60 is in a state of being housed inside the outer sheath 90 until the shaft 20 is inserted into a target part (i.e., target object). When the wire 61 is accommodated in the outer sheath 90, the outer sheath 90 is moved with respect to the shaft 20 toward the distal side, and a distal end portion of the outer sheath 90 is pressed against the proximal portion of the breaking member 60. Consequently, the sliding portion 50 is moved to the proximal side along the shaft 20, and the wire 61 is reduced in diameter so as to be accommodated inside the outer sheath 90. When the shaft 20 is inserted into the target part of the blood vessel, and then the outer sheath 90 is moved with respect to the shaft 20 toward the proximal side, and the breaking member 60 is exposed outside of the outer sheath 90 and is expanded by the breaking member's elastic force. In this case, the sliding portion 50 moves along the shaft 20 toward the distal side.

In accordance with an exemplary embodiment, it is desirable that the wire 61 is made of a shape-memory material, which is elastically deformable to a relatively high extent. The wire 61 materials can include, preferably, for example, a shape-memory alloy to which a shape-memory effect or superelasticity is imparted through heat treatment, for example, stainless steel, or the like. In accordance with an exemplary embodiment, the wire 61 material is preferably a Ni—Ti-based alloy, a Cu—Al—Ni-based alloy, a Cu—Zn—Al-based alloy, a combination of a Ni—Ti-based alloy, a Cu—Al—Ni-based alloy, and a Cu—Zn—Al-based alloy as the shape-memory alloy.

As illustrated in FIG. 1, the rotation-driving portion 70 includes a drive motor 71 and a gear portion 72 that links the drive motor 71 to the shaft 20. The drive motor 71 is rotated, and thereby the shaft 20 rotates in the circumferential direction. In the embodiment, the shaft 20 is driven by the drive motor 71 so as to rotate alternately in two positive and negative directions of the circumferential direction. Alternate rotation of the shaft 20 in the two positive and negative directions enables bloodstream to flow alternately in opposite directions.

Figure 11:
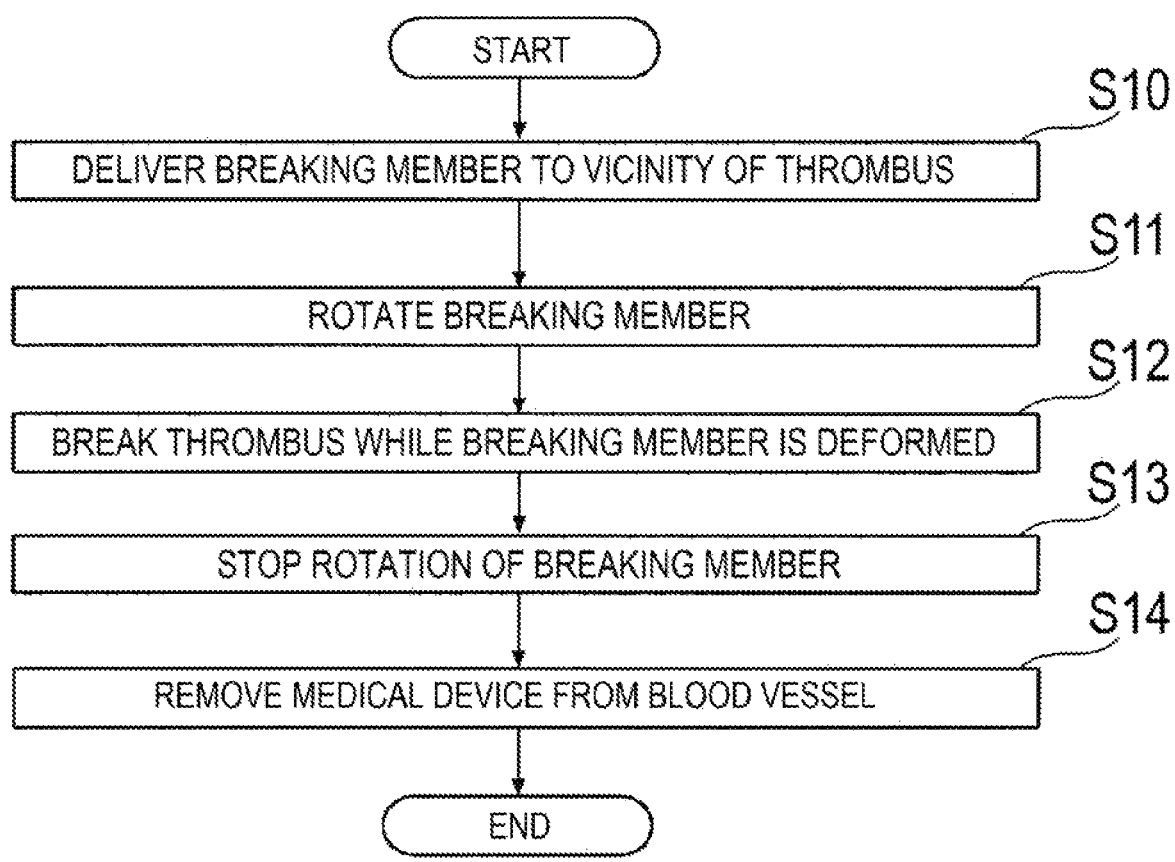
FIG. 11 is a flowchart for illustrating a procedure of using the medical device.

Next, a method of using the medical device 10 according to the first embodiment is described with an example of a case where the thrombus in the blood vessel is broken and aspirated, with reference to a flowchart illustrated in FIG. 11.

Figure 6A:
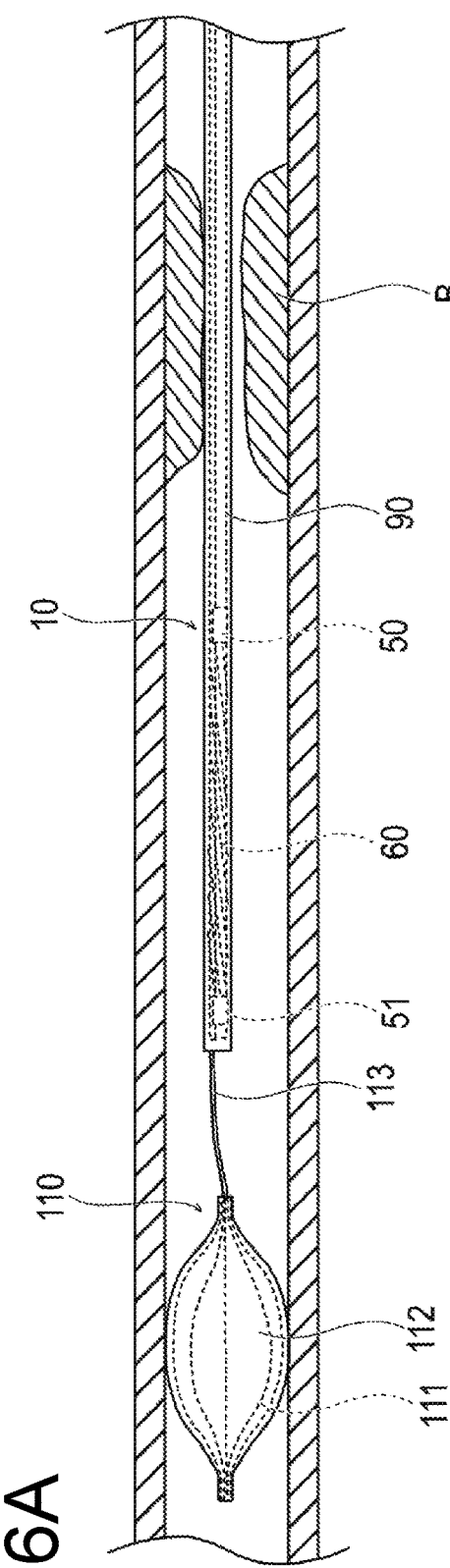

Before the shaft 20 of the medical device 10 of the first embodiment is inserted, it is desirable that a protective member such as a filter or a balloon that limits circulation of a fluid in the blood vessel is disposed on a downstream side or proximal (side to which the bloodstream flows) from the thrombus in the blood vessel. As illustrated in FIG. 6A, the embodiment uses a filter device 110 that includes an elastic body 111 made of a wire that is expanded by its own elastic force by being pushed out from a sheath, a net-shaped or film-shaped filter 112 that is disposed on an outer peripheral surface of the elastic body 111, and a wire portion 113 that is connected to the elastic body 111. When the elastic body 111 pushed out from the sheath is expanded, and the filter 112 comes into contact with the blood vessel, the filter 112 limits circulation of blood. Consequently, it is possible to prevent the broken thrombus from flowing in the blood vessel and moving to another position or portion of the blood vessel.

Figure 6B:
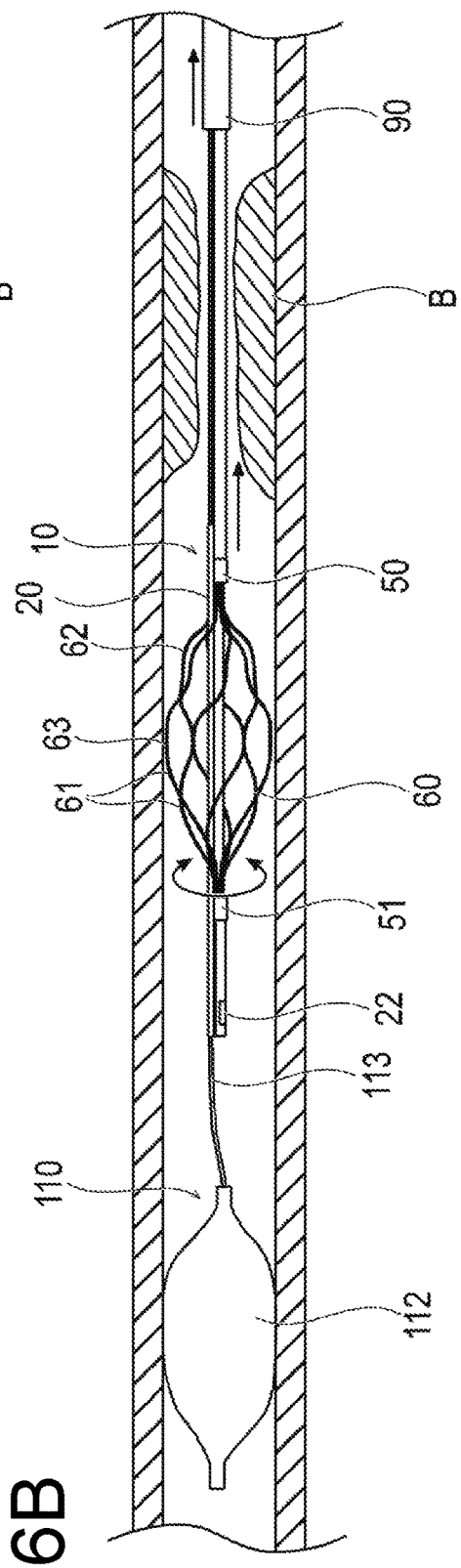

Next, the medical device 10 which is in a state in which the distal portion of the shaft 20 including the breaking member 60 is housed in the outer sheath 90 is prepared. Next, a proximal-side end portion of the wire portion 113 is inserted into the guide wire lumen of the guide wire housing 40 of the medical device 10. Next, the medical device 10 is caused to reach a distal side of a thrombus B with the wire portion 113 as a guide (Step S10). Then, when the outer sheath 90 is moved with respect to the shaft 20 toward the proximal side, the breaking member 60 is exposed outside the outer sheath 90 and the breaking member 60 is expanded by the elastic force of the breaking member 60, as illustrated in FIG. 6B. In this case, the sliding portion 50 moves with respect to the shaft 20 toward the distal side.

Next, when the rotation-driving portion 70 (refer to FIG. 1) rotates the shaft 20, in a state in which the breaking member 60 is in contact with the thrombus B or in a state in which the breaking member approaches the thrombus B, the breaking member 60 also rotates along with rotation of the shaft 20 (Step S11). In this case, the breaking member 60 is in the expanded state, and thus, the first soft contact portion 62 of the wire 61 is located most outward. Therefore, even when the breaking member 60 rotates, the first soft contact portion 62 comes into contact with a normal blood vessel (body lumen tissue), and the second hard contact portion 63 is unlikely to come into contact with the normal blood vessel. Therefore, damage to the blood vessel can be suppressed.

When the breaking member 60 enters a gap of the thrombus B, which is a low patency rate, the breaking member 60 is pressed by the thrombus B so as to come into the contracted state. Consequently, as illustrated in FIG. 7A, the second contact portion 63 projects more radially outward than the first contact portion 62. Therefore, when the breaking member 60 rotates, the breaking member 60 is deformed such that the second contact portion 63 that is relatively more rigid than the first contact portion 62 comes into contact with the thrombus B, and it is possible to break the thrombus B relatively effectively (Step S12). Since the second contact portion 63 is located in a proximal portion of the breaking member 60, the breaking member 60 moves toward the proximal side, and thereby the second contact portion 63 is likely to come into contact with the thrombus B. Therefore, it is possible to break the thrombus B rather efficiently. Incidentally, in accordance with an exemplary embodiment, a part of the breaking member that breaks (i.e., contacts) the thrombus is not limited only to the second contact portion 63.

Figure 8A:
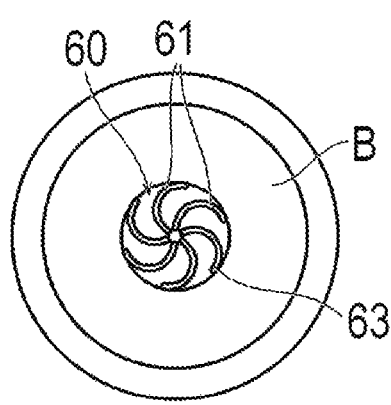
Figure 8B:
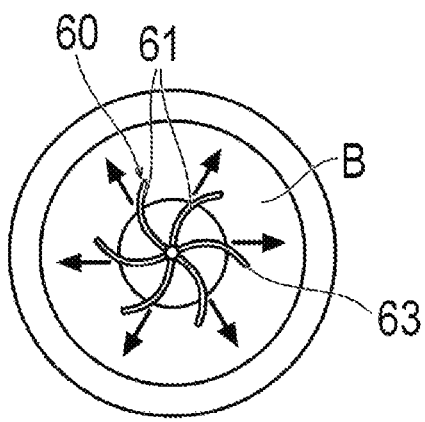
Figure 8C:
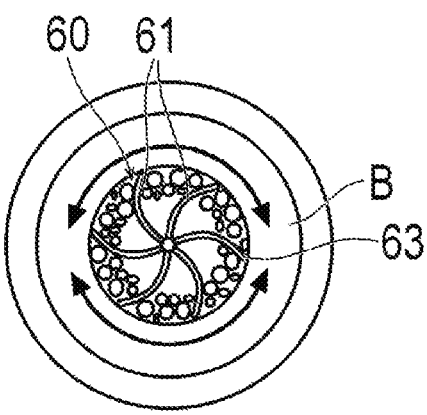
Figure 8D:
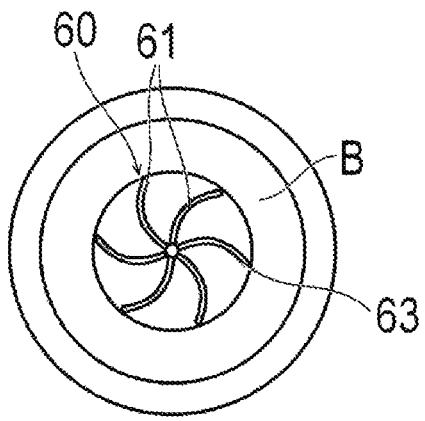

When the breaking member 60 repeats reciprocating rotation to the inside of the gap of the thrombus B in the positive and negative directions, there is a moment of switching from the state in which the breaking member 60 rotates, as illustrated in FIG. 8A, to a state in which the rotation of the breaking member 60 is stopped as illustrated in FIG. 8B. In order to change the rotating direction, the rotation is stopped or is slowed to a relatively low speed, and thereby the wire 61 is expanded in order to reduce a reaction force received from the thrombus B during rotation, and the second contact portion 63 of the wire 61 breaks into (i.e., contacts) the thrombus B. In this case, the second contact portion 63 curves into the radially outward convex shape in the contracted state, and thus the second contact portion easily breaks into (i.e., contacts) the thrombus B. Therefore, the second contact portion 63 rotates after breaking into the thrombus B, and thereby, as illustrated in FIGS. 8C and 8D, the second contact portion 63 is capable of scraping the thrombus B and breaking the thrombus rather effectively. In addition, in the contracted state, the second contact portion 63 curves into the convex shape toward the circumferential direction (rotating direction) of the breaking member 60. Therefore, the second contact portion 63 rotates, thereby, being capable of breaking into (i.e., entering) the thrombus B and breaking the thrombus B rather effectively. The breaking member 60 repeats rotation and stopping, thereby, breaking into the thrombus B during the stopping and repeating an operation of scraping the thrombus through rotation. Consequently, the breaking member 60 is capable of rapidly scraping a large amount of thrombus B. Incidentally, the breaking member 60 may not perform reciprocating rotation but may repeat rotating only in one direction and stopping. Even in this case, the breaking member 60 is capable of breaking into the thrombus B during the stopping and repeating an operation of scraping the thrombus through rotation. In a case where the breaking member 60 rotates only in one direction, the rotation may not be completely stopped but may be only slowed.

Figure 9A:
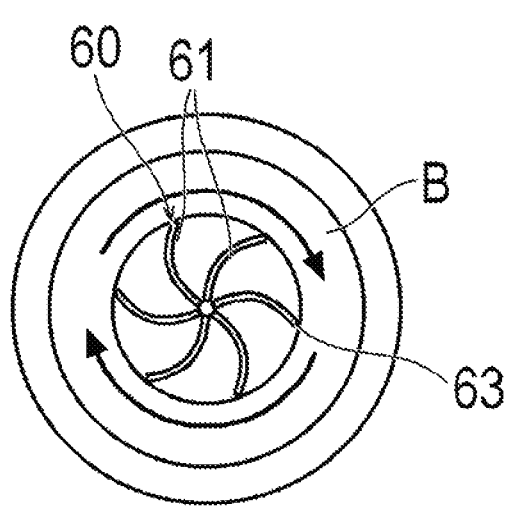
Figure 9B:
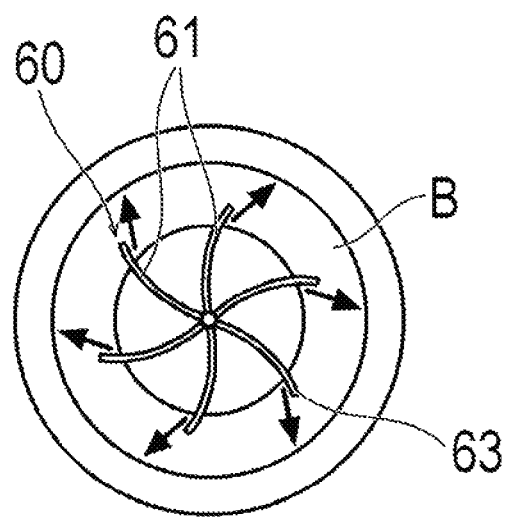
Figure 10A:
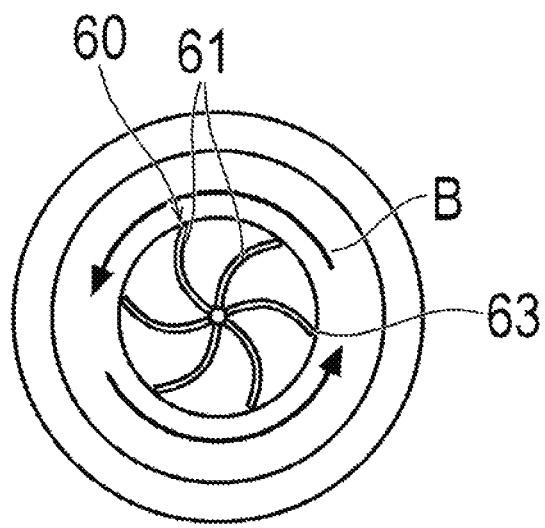
Figure 10B:
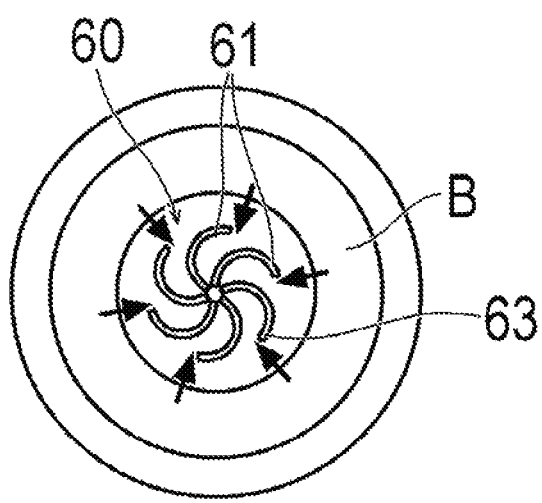

In accordance with an exemplary embodiment, the second contact portion 63 projects toward the circumferential direction (rotating direction). Therefore, as illustrated in FIG. 9A, when the breaking member rotates in a projecting direction, as illustrated in FIG. 9B, the breaking member 60 breaks into the thrombus B while being expanded. In accordance with an exemplary embodiment, the breaking member 60 breaks into the thrombus, thereby, being capable of scraping a large amount of thrombus B through agitation. In addition, the second contact portion 63 projects toward the circumferential direction (rotating direction). Therefore, as illustrated in FIG. 10A, when the breaking member rotates in a reverse direction of the projecting direction, as illustrated in FIG. 10B, the breaking member 60 is contracted. Consequently, the second contact portion 63 is rather easily separated from the thrombus B, and it is relatively easy for the breaking member 60 to move in the axial direction. In this manner, the reciprocating rotation of the breaking member 60 is repeated, and thereby it is possible to repeat scraping of the thrombus B and moving in the axial direction rather effectively.

While the reciprocating rotation of the breaking member 60 is repeated, reciprocating in the axial direction is repeated, and thereby the second contact portion 63 can gradually break the thrombus B in the blood vessel. When the thrombus B is gradually scraped, and the patency rate (i.e., likelihood that the blood vessel will remain open) of the blood vessel increases, the breaking member 60 is gradually expanded. When the breaking member 60 gradually approaches the expanded state, the first contact portion 62 is located more radially outward than the second contact portion 63 at a predetermined stage. Hence, as the thrombus B is removed, and a possibility of causing damage to the blood vessel increases, the first soft contact portion 62 is located radially outward, which makes it possible to prevent damage to the blood vessel.

When the breaking member 60 is moved in the rotating and axial directions in order to crush the thrombus, it is possible to connect the syringe 100 that accommodates a thrombolytic agent to the side tube 91 on the hand side (proximal side) of the outer sheath 90. While the breaking member 60 breaks the thrombus B, it is possible to push a plunger of the syringe 100 and eject the thrombolytic agent from the distal-side end portion of the outer sheath 90. The ejection of the thrombolytic agent may be performed continuously or intermittently, and it is possible to optionally change an ejection speed or an ejection amount, also. In a case where the thrombolytic agent is intermittently ejected, it is possible to perform aspiration while the ejection is stopped.

While the breaking member 60 breaks the thrombus, a solubilizer (i.e., an agent that increases the solubility of a substance) is ejected, and thereby it is possible to impregnate (i.e., fill), with the solubilizer, the gap of the thrombus which is generated by the breaking member 60 by a breaking effect. Therefore, it is possible to soften the thrombus before breaking or to decrease a volume of the thrombus by dissolution. In addition, dissolution of the broken thrombus is also effective for decreasing an amount of aspiration for discharging the thrombus later.

In accordance with an exemplary embodiment, the broken thrombus B is received (i.e., captured) by a filter device 110. Then, the aspirating syringe 100 (refer to FIG. 1) pulls the plunger and causes a pressure inside the outer sheath 90 to come into a negative pressure state. Consequently, the broken thrombus B can be aspirated from an opening portion on the distal side of the outer sheath 90 and the thrombus B can be discharged from the blood vessel.

After the aspiration of the thrombus B is completed, the rotational movement of the shaft 20 is stopped (Step S13). Next, the breaking member 60 is accommodated in the outer sheath 90, and the medical device 10 is removed from the blood vessel. Then, the filter device 110 is accommodated in the sheath or the like, is removed from the blood vessel, and the treatment is completed (Step S14).

As described above, the medical device 10 according to the embodiment is a device that is inserted into the body lumen so as to break the thrombus B (object) in the body lumen, the medical device including: the elongated shaft 20 that is rotatably driven; and the deformable breaking member 60 that is connected to the shaft 20 so as to be rotatable and extends along the shaft 20. The breaking member 60 has the first contact portion 62 and the second contact portion 63. The first contact portion 62 is located most outward in the radial direction of the breaking member 60 in a state in which the breaking member 60 is expanded toward the outer side in the radial direction. In the contracted state rather than the expanded state, the second contact portion 63 is located more outward in the radial direction of the breaking member 60 than the first contact portion 62.

In a case where a large amount of the thrombus B which is the breaking target is present and the patency rate (i.e., likelihood that the blood vessel will remain open) is relatively low, the breaking member 60 in the medical device 10 configured as described above will be contracted so that the second contact portion 63 is located outside and the second contact portion 63 comes into contact with the thrombus B, which makes it possible to break the thrombus B rather efficiently. In a case where a small amount of the thrombus B which is the breaking target is present and the patency rate is relatively high, the breaking member 60 comes into the expanded state so that the first contact portion 62 is located most outward and the first contact portion 62 comes into contact with the thrombus B, which makes it possible to reduce the burden on the blood vessel caused by the rotation of the breaking member 60.

In accordance with an exemplary embodiment, the first contact portion 62 is located more outward in the radial direction of the breaking member 60 than the second contact portion 63 in the natural state in which the breaking member 60 is expanded toward the outer side in the radial direction without an action of an external force. In this manner, while in the natural state, the first contact portion 62 is located reliably more outward in the radial direction of the breaking member 60 than the second contact portion 63, and thus the first contact portion 62 can be located more outward in the radial direction of the breaking member 60 than the second contact portion 63 in a state in which the breaking member 60 is expanded toward the outer side in the radial direction.

In accordance with an exemplary embodiment, the second contact portion 63 is relatively more rigid than the first contact portion 62. Consequently, in a case where a relatively large amount of the thrombus B (i.e., breaking target) is present and the patency rate is relatively low, the breaking member 60 is contracted so that the second contact portion 63, which is relatively more rigid than the first contact portion 62, is located more outward. Therefore, the second hard contact portion 63 is capable of coming into contact with the thrombus B, which makes it possible to break the thrombus B rather efficiently. In a case where the small amount of the thrombus B (i.e., breaking target) is present, and the patency rate is relatively high, the breaking member 60 comes into the expanded state so that the first contact portion 62, which is less rigid than the second contact portion 63, is located most outward. Therefore, it is possible to suppress an occurrence of contact of the second more rigid contact portion 63 with the blood vessel, and thus it is possible to reduce the burden on the blood vessel by the rotation of the breaking member 60.

In accordance with an exemplary embodiment, the first contact portion 62 has a shape different from that of the second contact portion 63. Consequently, the first contact portion 62 and the second contact portion 63 can cause different forces from each other to be applied to the contact target.

In accordance with an exemplary embodiment, the first contact portion 62 is located closer to the center portion of the breaking member 60 in the axial direction than the second contact portion 63 in the expanded state. Consequently, in the contracted state, even in a structure in which the second contact portion 63 is located most outward in the radial direction of the breaking member 60, the first contact portion 62 that is closer to the center portion than the second contact portion 63 can move toward the outermost side by bending of the wire 61 in the expanded state.

In accordance with an exemplary embodiment, the second contact portion 63 curves to have the curvature radius smaller than that of the fourth contact portion 62B included in the first contact portion 62 in the expanded state. Consequently, the second contact portion 63 has a structure in which it is more difficult to be deformed against the applied force than the first contact portion 62, and thus it is possible to break the thrombus B rather efficiently.

In accordance with an exemplary embodiment, the second contact portion 63 curves to have the radially outward convex shape in the contracted state. Consequently, it is rather easy for the second contact portion 63 to break (enter) into the thrombus B in the contracted state, and thus the second contact portion rotates, thereby, being capable of breaking the thrombus B rather effectively.

In accordance with an exemplary embodiment, the second contact portion 63 curves to have the convex shape toward the rotating direction in the contracted state. Consequently, the second contact portion 63 rotates, thereby, being capable of strongly breaking into the thrombus B and breaking and scraping the thrombus B rather effectively.

In accordance with an exemplary embodiment, positions of the connection portion on the distal side and the connection portion on the proximal side, in which the wire 61 is connected to the shaft 20, are different from each other in the circumferential direction. Consequently, since the wire 61 has a spiral shape overall, a contact area with the body lumen tissue increases, and thus it is possible for the first less rigid contact portion 62 to come into smooth contact with the body lumen tissue. In addition, the wire 61 has the spiral shape, and thereby it is rather easy to control the acting force from the rotating direction. Therefore, it is possible for the second more rigid contact portion 63 to break the thrombus B rather effectively.

In accordance with an exemplary embodiment, the wire 61 has the inflection point 66 between the first contact portion 62 and the second contact portion 63 in the expanded state. Consequently, the first contact portion 62 and the second contact portion 63 curve in different directions from each other, and thus it is possible to have different actions from each other with respect to the contact target (i.e., thrombus B).

In accordance with an exemplary embodiment, the medical device 10 according to the embodiment is a device that is inserted into the body lumen so as to break the thrombus B (object) in the body lumen, the medical device including: the elongated shaft 20 that is rotatably driven; and the breaking member 60 that is connected to the shaft 20 so as to be rotatable and has a plurality of deformable wires 61 that are arranged in the circumferential direction while extending along the shaft 20. The plurality of wires 61 are each provided with the first contact portion 62 and the second contact portion 63 that is more rigid than the first contact portion 62. In the medical device 10 configured as described above, it is possible to break the thrombus B which is the breaking target efficiently by the second contact portion 63 that is more rigid than the first contact portion 62. It is possible to reduce the burden on the blood vessel by the rotation of the breaking member 60 with the first contact portion 62 less rigid than the second contact portion 63.

In addition, the disclosure also provides a treatment method for breaking the thrombus (object) in the body lumen by using the medical device 10 described above. The method includes Step S10 of inserting the shaft 20 into the body lumen and delivering the breaking member 60 to the vicinity of the thrombus B; and Step S12 of inserting the breaking member 60 into the gap of the thrombus B and rotating the breaking member 60 by the shaft 20 so as to break the thrombus B while deforming the breaking member 60 due to own elastic force depending on the size of the gap of the thrombus B so as to change the contact position with the thrombus B between the first contact portion 62 or the second contact portion 63 in the radial direction. In a case where a large amount of the thrombus B is present and the patency rate is relatively low, the breaking member 60 is contracted in the step of breaking the thrombus B in the treatment method configured as described above so that the second contact portion 63, which is more rigid than the first contact portion 62, is located most outward to come into contact with the thrombus B, which makes it possible to break the thrombus B rather efficiently. In a case where a small amount of the thrombus B which is the breaking target is present and the patency rate is relatively high, the breaking member 60 comes into the expanded state so that the first contact portion 62 is located most outward, which makes it possible to reduce the burden on the blood vessel caused by the rotation of the breaking member 60.

Second Embodiment

In accordance with an exemplary embodiment, a medical device according to a second embodiment differs from the medical device 10 according to the first embodiment only in that a breaking member 200 is provided. Incidentally, the same reference signs are assigned to parts having the same functions as those of the first embodiment, and thus the description of those same reference signs and same functions is omitted.

Figure 12:
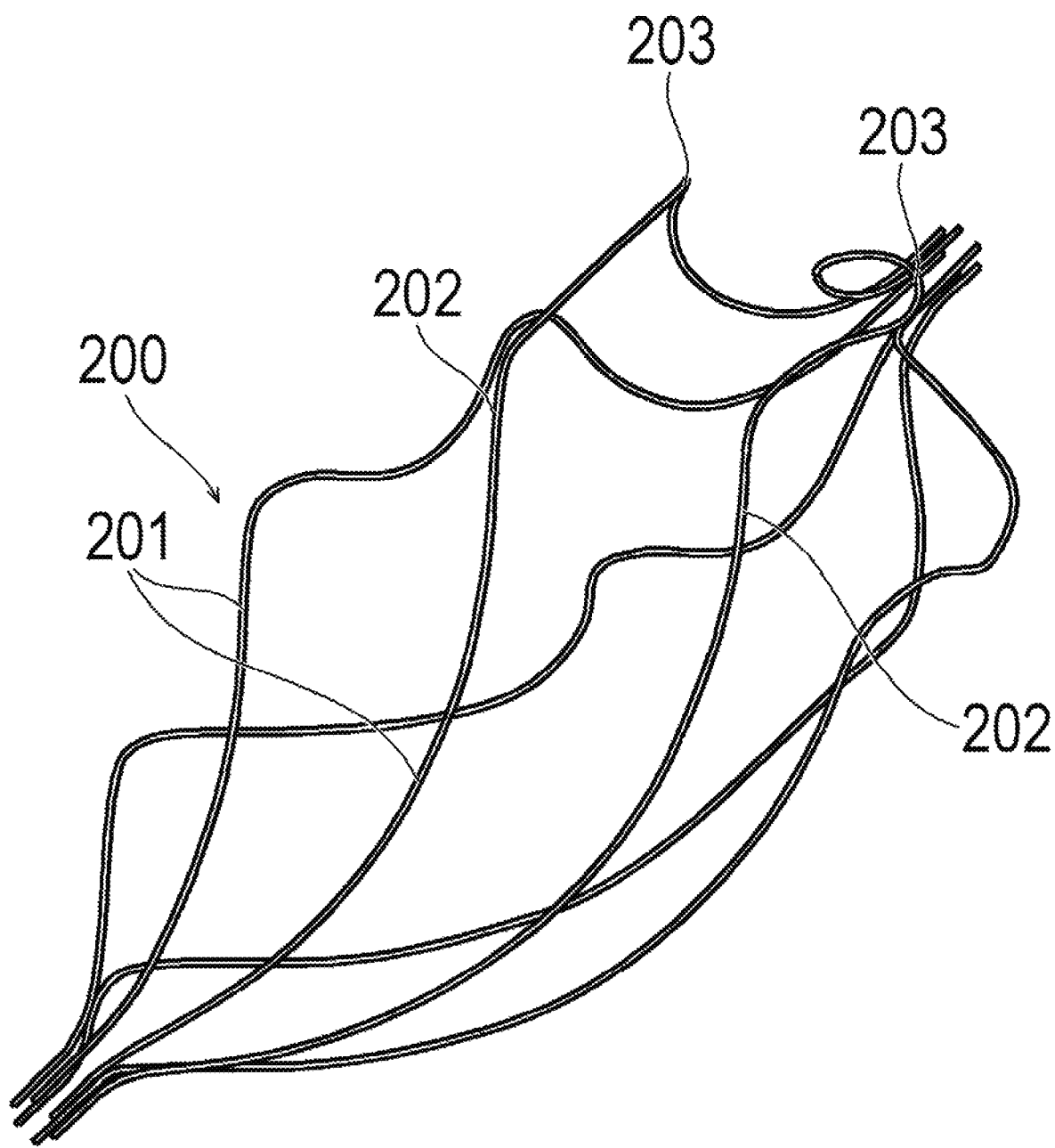
FIG. 12 is a perspective view illustrating a breaking member of a medical device according to a second embodiment.
Figure 14A:
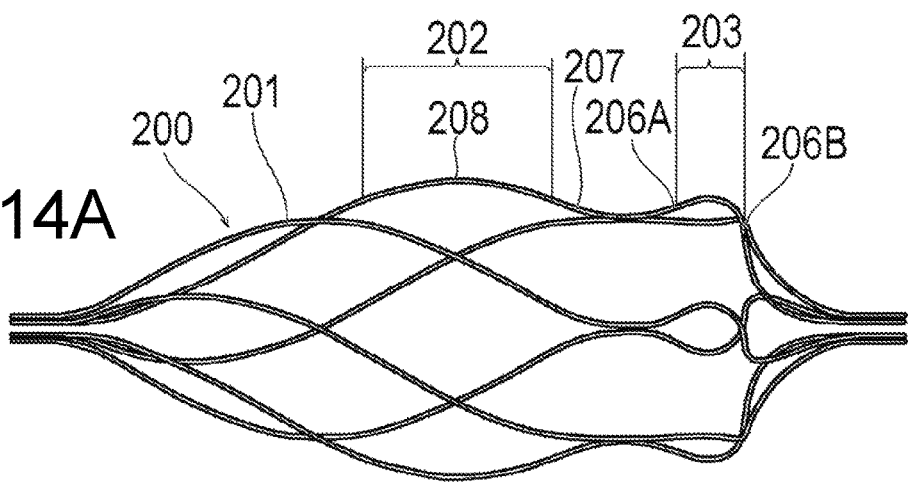
Figure 15A:
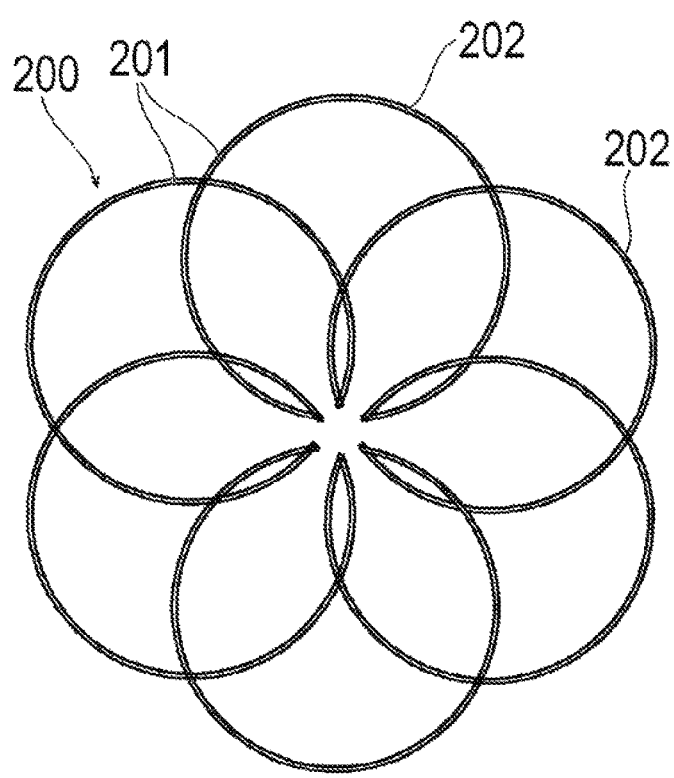

In accordance with an exemplary embodiment, the breaking member 200 has a plurality of (in the embodiment, six) wires 201. Incidentally, the number of wires 201 is not particularly limited. As illustrated in FIGS. 12, 14A, and 15A, in the expanded state in which the breaking member 200 is expanded radially outward, each of the wires 201 has a first contact portion 202 that is located on the outermost side in the radial direction. The first contact portion 202 is located in a part of the breaking member 200 having the largest outer diameter in the axial direction. In the expanded state, the first contact portion 202 is a part that is located more radially outward than a second contact portion 203 of the breaking member 200 to be described below. The first contact portion 202 is located closer to the center portion of the breaking member 200 in the axial direction than the second contact portion 203. A shape of each of the wires 201 in the expanded state is substantially identical with a shape of the each of the wires 201 in the natural state in which no external force acts on each of the wires 201. Hence, the wires 201 are formed into a shape in the expanded state through a heat treatment in advance.

Figure 13:
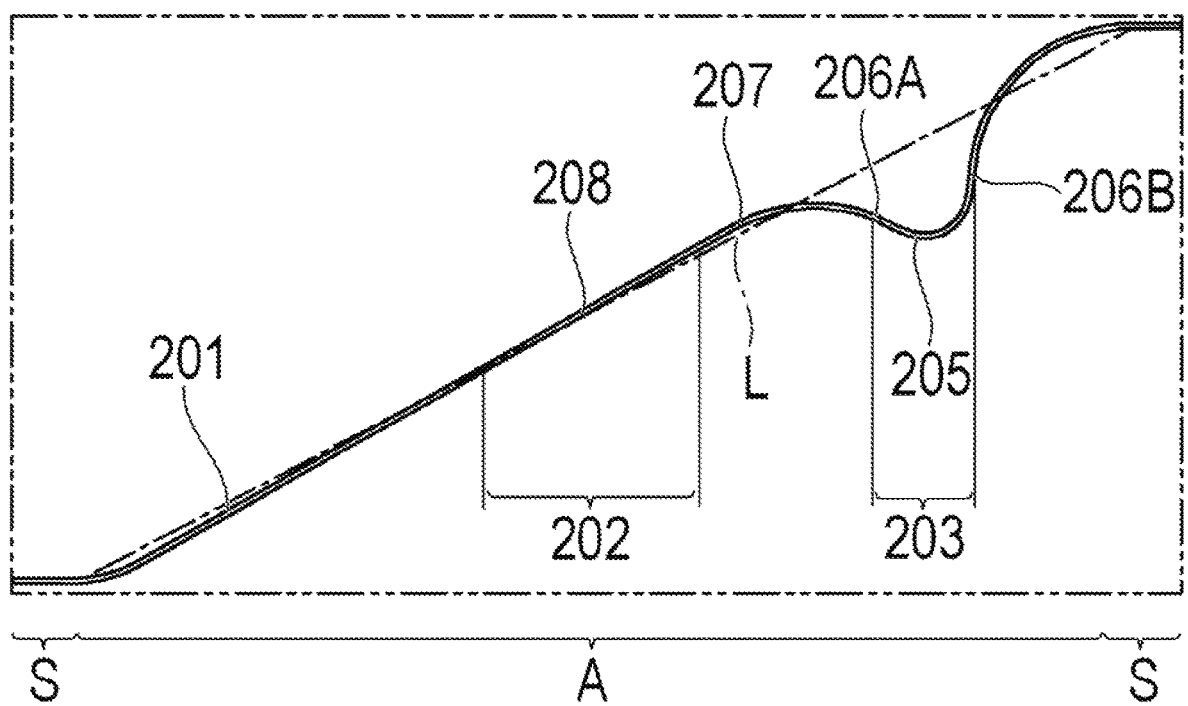
FIG. 13 is a developed view in a circumferential direction of a wire that configures the breaking member of the second embodiment.

In addition, as illustrated in FIG. 13, in a developed view in the circumferential direction in the expanded state, each of the wires 201 has one convex portion 205 on the proximal side in the range A excluding the fixing range S for fixing to the sliding portion 50 or the fixing portion 51. In accordance with an exemplary embodiment, the convex portion 205 projects, for example, by approximately 6 mm in a three-dimensional manner. Each of the wires 201 has a first inflection point 206A on the distal side of the convex portion 205 and a second inflection point 206B on the proximal side of the convex portion 205. In accordance with an exemplary embodiment, each of the wires 201 may have more inflection points. In addition, each of the wires 201 has a transition portion 207 in which a straight line and a curve intersect each other in the developed view in the circumferential direction, more on the distal side than the first inflection point 206A. Each of the wires 201 has a vertex 208, at which the largest outer diameter increases in the expanded state, more on the distal side from the transition portion 207.

In accordance with an exemplary embodiment, the second contact portion 203 is a range from the first inflection point 206A to the second inflection point 206B. Hence, the second contact portion 203 has the convex portion 205. The transition portion 207 is separated from the reference line L in the circumferential direction. In the expanded state, the first contact portion 202 is located more radially outward than the second contact portion 203 and can be straight line-shaped in the developed view in the circumferential direction. In accordance with an exemplary embodiment, in the developed view in the circumferential direction, the first contact portion may have only a curve or may have a curve and a straight line.

Figure 14B:
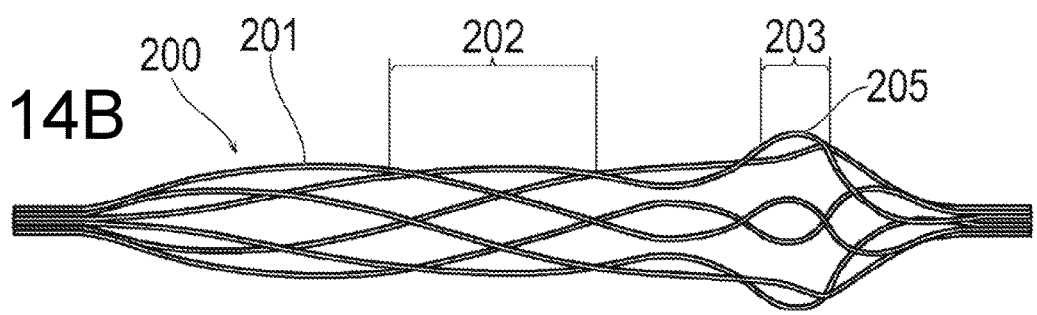
Figure 15B:
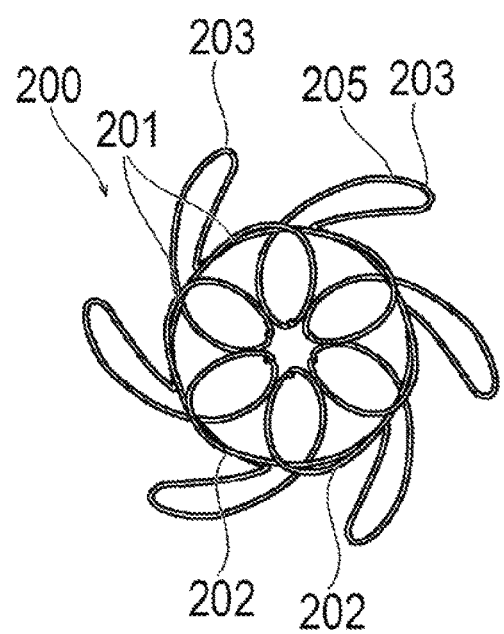

In the contracted state in which the breaking member 200 is more contracted radially inward from the expanded state, each of the wires 201 has the second contact portion 203 on the outermost side in the radial direction, as illustrated in FIGS. 14B and 15B. The second contact portion 203 is configured of the convex portion 205 (refer to FIG. 9). In the three dimensional view, the second contact portion 203 may have the curvature radius smaller than that of the first contact portion 202. In accordance with an exemplary embodiment, the second contact portion 203 has a projecting length longer than that of the second contact portion 63 in the first embodiment. In the contracted state, the first contact portion 202 is contracted to be smaller than the second contact portion 203 in the radial direction. In other words, when the first contact portion 202 is located close to the center portion of the breaking member 200 in the axial direction, and thus the breaking member 200 is stretched in the axial direction, thereby, being contracted in the radial direction, the first contact portion approaches an outer surface of the shaft 20 more than the second contact portion 203. Further, the second contact portion 203 has a curvature radius smaller than a curvature radius of the first contact portion 202, and thus the second contact portion 203 is more unlikely to extend in a straight line shape than the first contact portion 202. Further, the end portion of the breaking member 200 is fixed to the sliding portion 50 such that it is not possible to change the position and the orientation of the end portion, and thereby the second contact portion 203 that is closer to the end portion is influenced by the end portion such that the second contact portion is unlikely to be deformed and is unlikely to approach the outer surface of the shaft 20. Therefore, when the breaking member 200 is stretched in the axial direction, thereby, being contracted in the radial direction, the second contact portion 203 remains curved and thus the second contact portion 203 does not necessarily approach the shaft 20. Therefore, the second contact portion 203 is located more outward in the radial direction than the first contact portion 202.

In accordance with an exemplary embodiment, the first contact portion 202 and the second contact portion 203 curve in different directions from each other in the three dimensional view and have different curvature radius from each other. Therefore, it is possible to have different action with respect to the contact target (i.e., thrombus B). In the embodiment, in the contracted state, when viewed from the distal side, the convex portion 205 located in the second contact portion 203 is larger than the outer diameter of the first contact portion 202, and thereby the second contact portion 203 comes into strong contact with the thrombus B or the lumen tissue. Incidentally, the second contact portion 203 curves in a three-dimensional manner, and thus the shape of the second contact portion changes depending on a direction of view. In the contracted state, when viewed from the front surface, the second contact portion 203 is observed as a steep projecting portion having a small width so as to overlap the wire 201 in the axial direction (refer to FIG. 15B). In addition, in the contracted state, when viewed from side, the second contact portion 203 is observed as a gentle projecting portion having a larger width, compared with the case of being viewed from the front surface (refer to FIG. 14B). In the expanded state, the first contact portion 202 is formed to have a shape approximate to a straight line so as to come into smooth contact with the thrombus B or the lumen tissue.

In the three dimensional view, the second contact portion 203 has a curvature radius smaller than that of the first contact portion 202, and thus the second contact portion 203 has a structure in which it is relatively more difficult to be deformed against an applied force than the first contact portion 202. In addition, the end portion of the breaking member 200 is fixed to the sliding portion 50 such that it is not possible to change a position and an orientation of the end portion, and thereby the second contact portion 203 that is closer to the end portion than the first contact portion 202 is influenced by the end portion such that the second contact portion is unlikely to be deformed and is unlikely to approach the outer surface of the shaft 20. Hence, the second contact portion 203 has a relatively more rigid structure than that of the first contact portion 202 and has a relatively high breaking force and agitating force. Incidentally, in a three dimensional view, the first contact portion has the same curvature radius as that of the second contact portion; however, it is possible to generate different actions from each other with respect to the contact target (i.e., thrombus B).

In accordance with an exemplary embodiment, in the contracted state, the second contact portion 203 has the radially outward convex shape when viewed from the front surface, and the convex shape curves. Therefore, the second contact portion 203 rather easily breaks into (i.e., enters) the thrombus B in the body lumen in the contracted state. In addition, in the contracted state, the second contact portion 203 has the convex shape toward the circumferential direction (rotating direction) of the breaking member 200, and the convex shape curves. Therefore, the second contact portion 203 rotates, thereby, rather easily and strongly breaking into (i.e., entering) the thrombus B in the body lumen.

In accordance with an exemplary embodiment, the medical device according to the second embodiment has the second contact portion 203 larger than the second contact portion 63 in the first embodiment. Therefore, the medical device has a relatively higher breaking performance and agitating performance in the contracted state in which the second contact portion 203 is located more radially outward than the first contact portion 202.

Third Embodiment

A medical device according to a third embodiment differs from the medical device 10 according to the first embodiment only in that a breaking member 300 is provided. Incidentally, the same reference signs are assigned to parts having the same functions as those of the first embodiment, and thus the description of those same reference signs and same functions is omitted.

Figure 16:
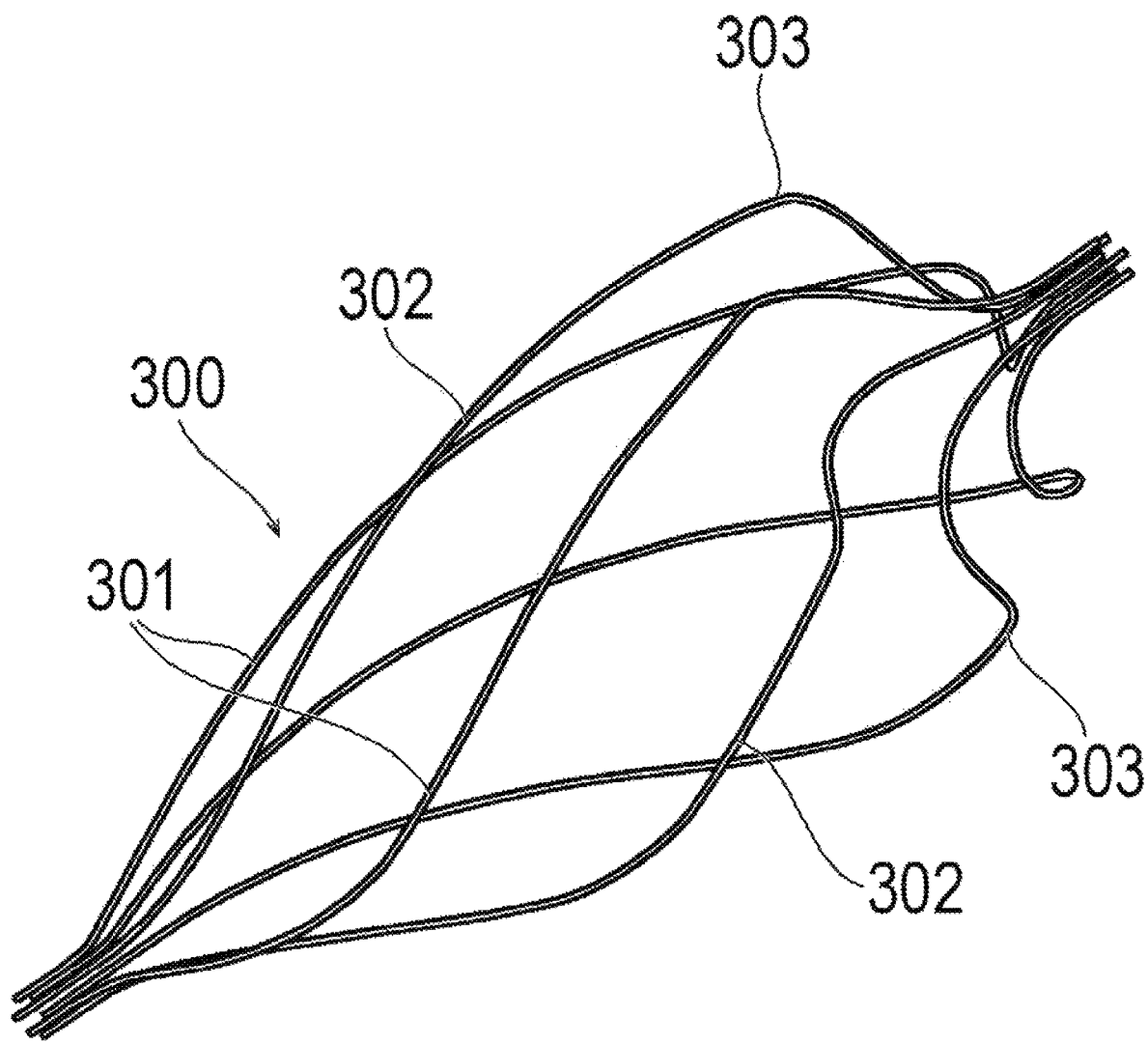
FIG. 16 is a perspective view illustrating a breaking member of a medical device according to a third embodiment.
Figure 18A:
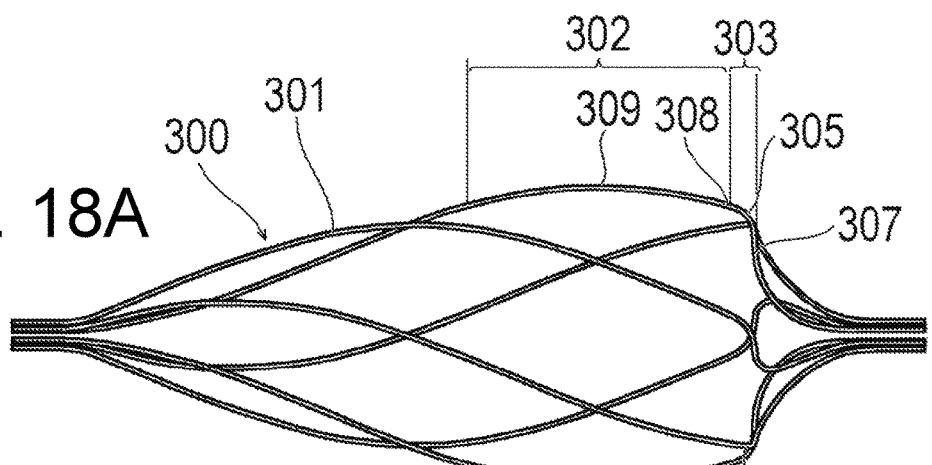
Figure 19A:
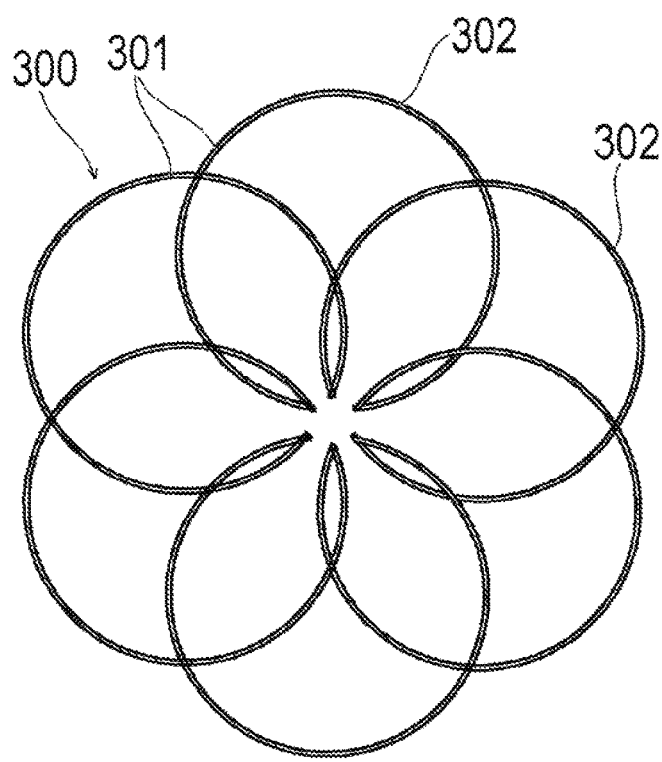

In accordance with an exemplary embodiment, the breaking member 300 has a plurality of (in the embodiment, six) wires 301. Incidentally, the number of wires 301 is not particularly limited. As illustrated in FIGS. 16, 18A, and 19A, in the expanded state in which the breaking member 300 is expanded radially outward, each of the wires 301 has a first contact portion 302 that is located on the outermost side in the radial direction. The first contact portion 302 is located in a part of the breaking member 300 having the largest outer diameter in the axial direction. In the expanded state, the first contact portion 302 is located more radially outward than the second contact portion 303 of the breaking member 300 to be described below. The first contact portion 302 is located to be closer to the center portion of the breaking member 300 in the axial direction than the second contact portion 303. In accordance with an exemplary embodiment, a shape of each of the wires 301 in the expanded state is substantially identical with a shape of each of the wires 301 in the natural state in which no external force acts on each of the wires 301. Hence, the wires 301 are formed into a shape in the expanded state through a heat treatment in advance.

Figure 17:
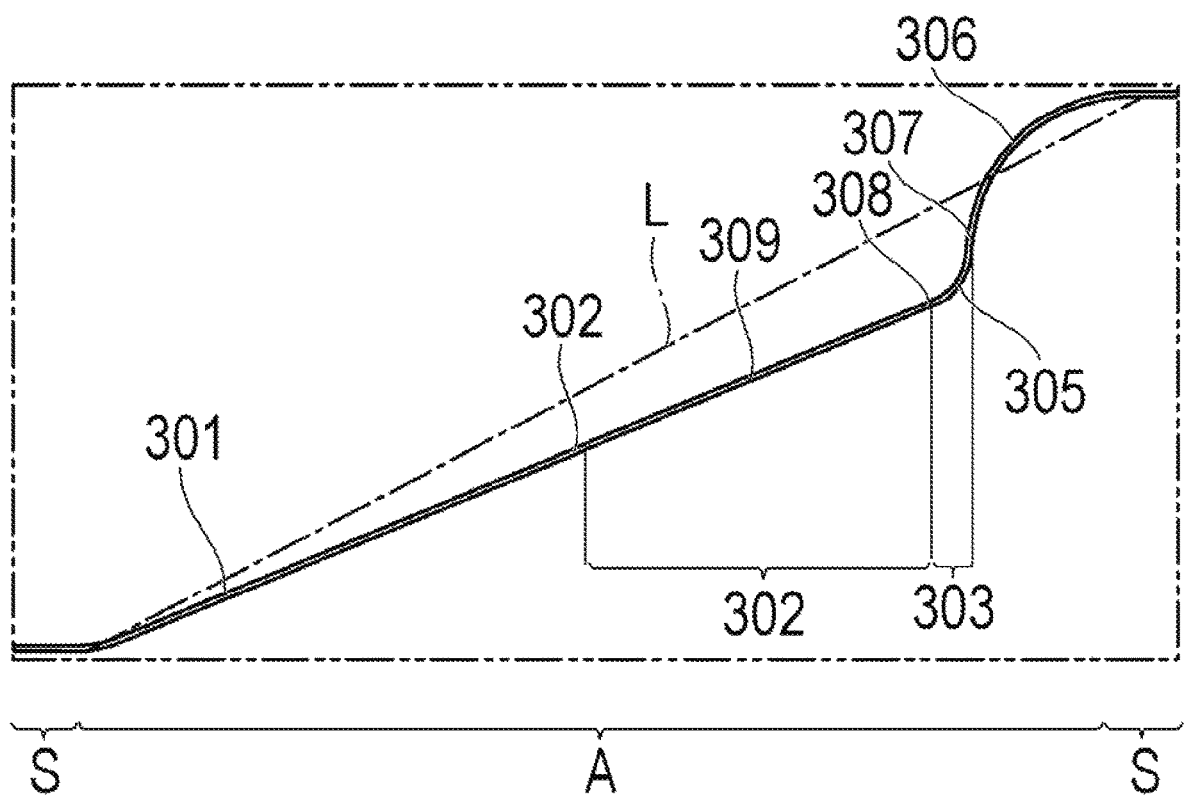
FIG. 17 is a developed view in a circumferential direction of a wire that configures the breaking member of the third embodiment.

In accordance with an exemplary embodiment, as illustrated in FIG. 17, in a developed view in the circumferential direction in the expanded state, each of the wires 301 has a first convex portion 305 and a second convex portion 306 that projects to curve toward an opposite side of the first convex portion 305, on the proximal side in the range A excluding the fixing range S for fixing to the sliding portion 50 or the fixing portion 51. In accordance with an exemplary embodiment, the first convex portion 305 projects, for example, by about 6 mm in a three-dimensional manner. Each of the wires 301 has an inflection point 307 between the first convex portion 305 and the second convex portion 306. In accordance with an exemplary embodiment, each of the wires 301 may have more inflection points. In addition, each of the wires 301 has a transition portion 308 in which a straight line and a curve intersect each other in the developed view in the circumferential direction, more on the distal side from the inflection point 307. Each of the wires 301 has a vertex 309, at which the largest outer diameter increases in the expanded state, more on the distal side from the transition portion 308.

In accordance with an exemplary embodiment, the second contact portion 303 is a range from the inflection point 307 to the transition portion 308. Hence, the second contact portion 303 has the first convex portion 305. In accordance with an exemplary embodiment, the second contact portion 303 is defined to have a range from the inflection point 307 to the transition portion 308; however, the second contact portion 303 is not limited to the range from the inflection point 307 to the transition portion 308, for example, the second contact portion 303 can be defined in a range including the first convex portion 305 and the second convex portion 306, for example. In the expanded state, the first contact portion 302 is located more radially outward than the second contact portion 303 and is straight line-shaped in the developed view in the circumferential direction. In accordance with an exemplary embodiment, in the developed view in the circumferential direction, the first contact portion may have only a curve or may have a curve and a straight line.

Figure 18B:
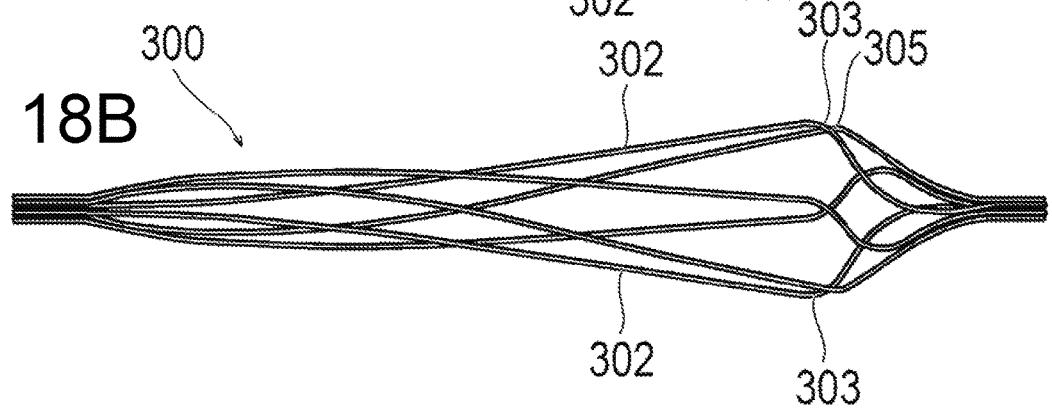
Figure 19B:
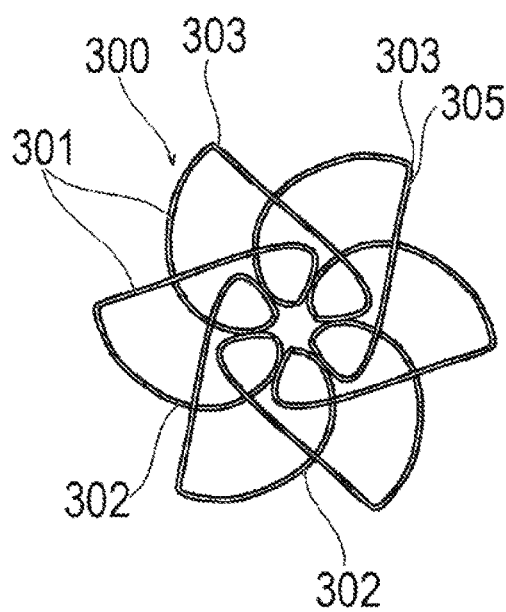

In the contracted state in which the breaking member 300 is more contracted radially inward from the expanded state, each of the wires 301 has the second contact portion 303 on the outermost side in the radial direction, as illustrated in FIGS. 18B and 19B. In accordance with an exemplary embodiment, the second contact portion 303 is configured of the first convex portion 305 (refer to FIG. 17). The second contact portion 303 has a curvature radius smaller than a curvature radius of the first contact portion 302. In accordance with an exemplary embodiment, the second contact portion 303 has a projecting length longer than that of the second contact portion 63 in the first embodiment. In the contracted state, the first contact portion 302 is contracted to be smaller than the second contact portion 303 in the radial direction. In accordance with an exemplary embodiment, when the first contact portion 302 is located close to the center portion of the breaking member 300 in the axial direction, and thus the breaking member 300 is stretched in the axial direction, thereby, being contracted in the radial direction, the first contact portion 302 approaches the outer surface of the shaft 20 more than the second contact portion 303. Further, the second contact portion 303 has a curvature radius smaller than a curvature radius of the first contact portion 302, and thus the second contact portion 303 is more unlikely to extend in a straight line shape than the first contact portion 302. Further, the end portion is fixed to the sliding portion 50 such that it is not possible to change a position and an orientation of the end portion, and thereby the second contact portion 303 that is close to the end portion is influenced by the end portion such that the second contact portion 303 is unlikely to be deformed and is unlikely to approach the outer surface of the shaft 20. Therefore, when the breaking member 300 is stretched in the axial direction, thereby, being contracted in the radial direction, the second contact portion 303 remains curved and thus the second contact portion 303 does not necessarily approach the shaft 20. Therefore, the second contact portion is located more outward in the radial direction than the first contact portion 302.

In accordance with an exemplary embodiment, the first contact portion 302 and the second contact portion 303 curve in different directions from each other in the three dimension and have a different curvature radius from each other. Therefore, it is possible to have different action with respect to the contact target, for example, thrombus B. In the embodiment, in the contracted state, when viewed from the distal side, the convex portion 305 located in the second contact portion 303 is larger than the outer diameter of the first contact portion 302, and thereby the second contact portion 303 comes into contact with the thrombus B or the lumen tissue. Incidentally, the second contact portion 303 curves in a three-dimensional manner, and thus the shape of the second contact portion changes depending on a direction of view. In the contracted state, when viewed from the front surface, the second contact portion 303 is observed as a steep projecting portion having a small width so as to overlap the wire 301 in the axial direction (refer to FIG. 19B). In addition, in the contracted state, when viewed from side, the second contact portion 303 is observed as a gentle projecting portion having a larger width, compared with the case of being viewed from the front surface (refer to FIG. 18B). In the expanded state, the first contact portion 302 is formed to have a shape approximate to a straight line so as to come into smooth contact with the thrombus B or the lumen tissue. In accordance with an exemplary embodiment, the convex portion of the second contact portion is not one curve and may have a plurality of different curves. In addition, the convex portion of the second contact portion may have a curve and a straight line, for example.

In the three dimensional view, the second contact portion 303 has the curvature radius smaller than that of the first contact portion 302, and thus the second contact portion has a structure in which it is more difficult to be deformed against an applied force than the first contact portion 302. In addition, the end portion of the breaking member 300 is fixed to the sliding portion 50 such that it is not possible to change a position and an orientation of the end portion, and thereby the second contact portion 303 that is closer to the end portion than the first contact portion 302 is influenced by the end portion such that the second contact portion is unlikely to be deformed and is unlikely to approach the outer surface of the shaft 20. Hence, the second contact portion 303 has a relatively more rigid structure than that of the first contact portion 302 and has a relatively high breaking force and agitating force. Incidentally, in a three dimensional view, the first contact portion has the same curvature radius as that of the second contact portion; however, it is possible to generate different actions from each other with respect to the contact target.

In accordance with an exemplary embodiment, in the contracted state, the second contact portion 303 has the radially outward convex shape when viewed from the front surface, and the convex shape curves. Therefore, the second contact portion 303 easily breaks (or enters) into the thrombus B in the body lumen in the contracted state. In addition, in the contracted state, the second contact portion 303 has the convex shape toward the circumferential direction (rotating direction) of the breaking member 300, and the convex shape curves. Therefore, the second contact portion 303 rotates, thereby, rather easily and strongly breaking into the thrombus B in the body lumen.

In accordance with an exemplary embodiment, the medical device according to the third embodiment has the second contact portion 303 larger than the second contact portion 63 in the first embodiment. Therefore, the medial device has relatively higher breaking performance and agitating performance in the contracted state in which the second contact portion 303 is located more radially outward than the first contact portion 302.

Fourth Embodiment

A medical device according to a fourth embodiment differs from the medical device 10 according to the first embodiment only in that a breaking member 400 is provided. Incidentally, the same reference signs are assigned to parts having the same functions as those of the first embodiment, and thus the description of those same reference signs and same functions is omitted.

Figure 20A:
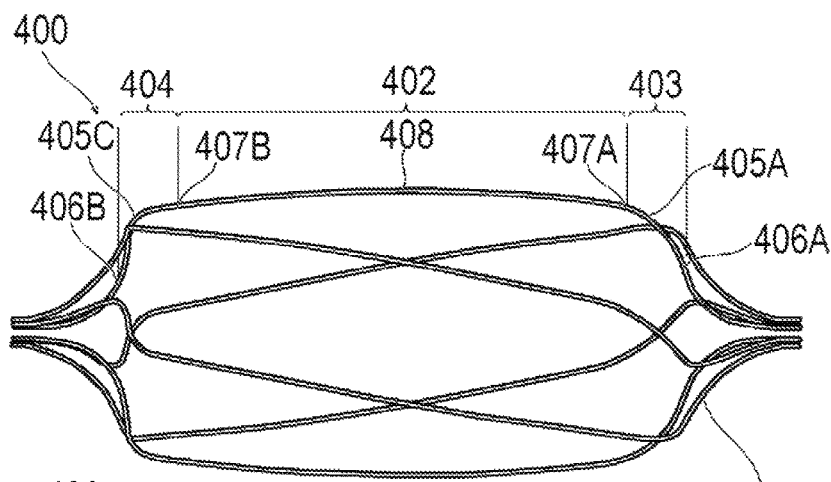

The breaking member 400 has a plurality of (in the embodiment, six) wires 401. Incidentally, the number of wires 401 is not particularly limited. As illustrated in FIG. 20A, in the expanded state in which the breaking member 400 is expanded radially outward, each of the wires 401 has a first contact portion 402 that is located on the outermost side in the radial direction. The first contact portion 402 is located in a part of the breaking member 400 having the largest outer diameter in the axial direction. In the expanded state, the first contact portion 402 is located more radially outward than a second contact portion 403 and a third contact portion 404 of the breaking member 400 to be described below. The first contact portion 402 is located to be closer to the center portion of the breaking member 400 in the axial direction than the second contact portion 403. A shape of each of the wires 401 in the expanded state is substantially identical with a shape of each of the wires 401 in the natural state in which no external force acts on each of the wires 401. Hence, the wires 401 are formed into a shape in the expanded state through a heat treatment in advance.

Figure 21:
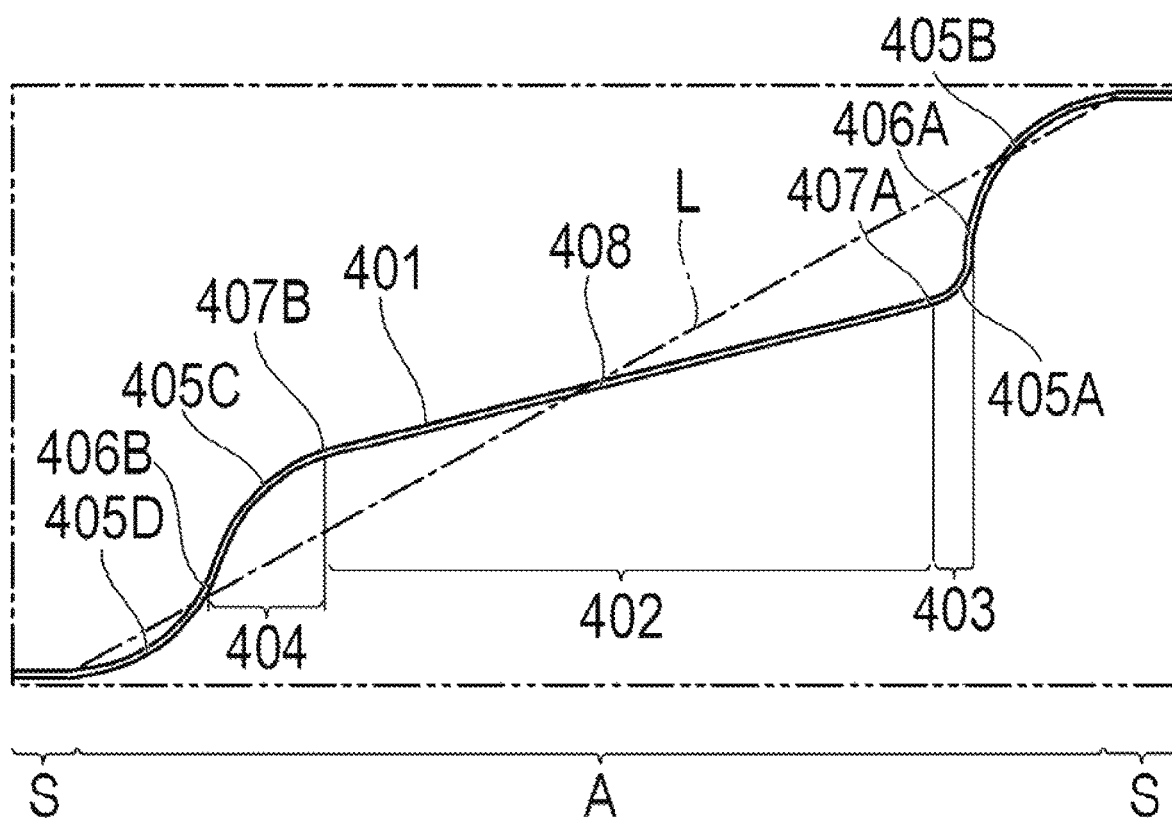
FIG. 21 is a developed view in a circumferential direction of a wire that configures the breaking member of the fourth embodiment.

In accordance with an exemplary embodiment, as illustrated in FIG. 21, in a developed view in the circumferential direction in the expanded state, each of the wires 401 has a first convex portion 405A and a second convex portion 405B that projects to curve toward an opposite side of the first convex portion 405A, on the proximal side in the range A excluding the fixing range S for fixing to the sliding portion 50 or the fixing portion 51. In accordance with an exemplary embodiment, each of the wires 401 has a third convex portion 405C and a fourth convex portion 405D that projects to curve toward an opposite side of the third convex portion 405C, on the distal side in the range A. The first convex portion 405A and the fourth convex portion 405D project toward the same side in the circumferential direction in the developed view in the circumferential direction. The second convex portion 405B and the third convex portion 405C project toward the same side in the circumferential direction in the developed view in the circumferential direction. Each of the wires 401 has a first inflection point 406A between the first convex portion 405A and the second convex portion 405B. In addition, each of the wires 401 has a second inflection point 406B between the third convex portion 405C and the fourth convex portion 405D. In accordance with an exemplary embodiment, each of the wires 401 may have more inflection points. In addition, each of the wires 401 has a first transition portion 407A in which a straight line and a curve intersect each other in the developed view in the circumferential direction, more on the distal side than the first convex portion 405A. In addition, each of the wires 401 has a second transition portion 407B in which a straight line and a curve intersect each other in the developed view in the circumferential direction, more on the proximal side than the third convex portion 405C. Each of the wires 401 has a vertex 408, at which the largest outer diameter increases in the expanded state, in a range from the first transition portion 407A and the second transition portion 407B.

The second contact portion 403 is a range from the first inflection point 406A to the first transition portion 407A. Hence, the second contact portion 403 has the first convex portion 405A. In accordance with an exemplary embodiment, the second contact portion 403 is defined to have a range from the first inflection point 406A to the first transition portion 407A; however, the second contact portion 403 is not limited to the range from the first inflection point 406A to the first transition portion 407A, and it is possible to define the second contact portion 403 in a range including the first convex portion 405A and the second convex portion 4056, for example.

The third contact portion 404 is a range from the second inflection point 406B to the second transition portion 407B. Hence, the third contact portion 404 has the third convex portion 405C. In accordance with an exemplary embodiment, the third contact portion 404 is defined to have a range from the second inflection point 406B to the second transition portion 407B; however, the third contact portion 403 is not limited to the second inflection point 406B to the second transition portion 470B, and it is possible to define the third contact portion 404 in a range including the third convex portion 405C and the fourth convex portion 405D, for example.

In accordance with an exemplary embodiment, the first contact portion 402 is located between the first transition portion 407A and the second transition portion 407B in the expanded state and is a straight line in the developed view in the circumferential direction. In accordance with an exemplary embodiment, in the developed view in the circumferential direction, the first contact portion may have only a curve or may have a curve and a straight line.

Figure 20B:
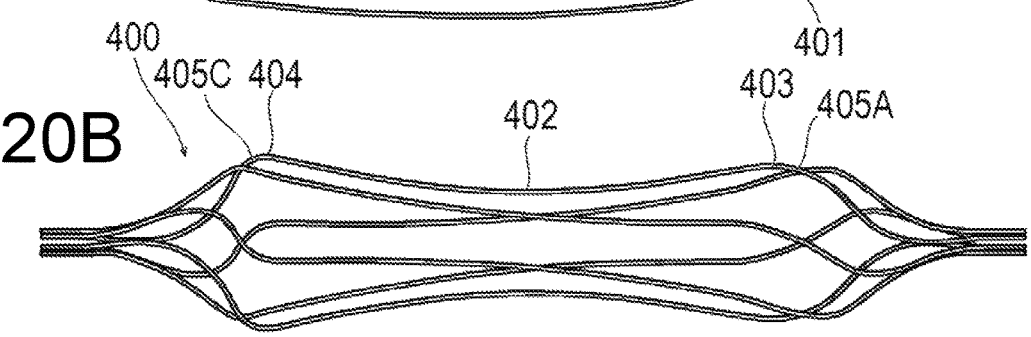

In the contracted state in which the breaking member 400 is more contracted radially inward from the expanded state, each of the wires 401 has the second contact portion 403 and the third contact portion 404 which are located more on the outer side in the radial direction than the first contact portion 402, as illustrated in FIG. 20B. The second contact portion 403 has the first convex portion 405A. The second contact portion 403 has the curvature radius smaller than the curvature radius of the first contact portion 402. The third contact portion 404 has the third convex portion 405C. The third contact portion 404 has the curvature radius smaller than the curvature radius of the first contact portion 402. In the contracted state, the first contact portion 402 is contracted to be smaller than the second contact portion 403 and the third contact portion 404, in the radial direction. In accordance with an exemplary embodiment, when the first contact portion 402 is located close to the center portion of the breaking member 400 in the axial direction, and thus the breaking member 400 is stretched in the axial direction, thereby, being contracted in the radial direction, the first contact portion 402 approaches an outer surface of the shaft 20 more than the second contact portion 403 and the third contact portion 404. Further, the second contact portion 403 and the third contact portion 404 have a curvature radius smaller than a curvature radius of the first contact portion 402, and thus the second contact portion 403 and the third contact portion 404 are more unlikely to extend in a straight line shape than the first contact portion 402. Further, the second contact portion 403 and the third contact portion 404 which are closer to the end portion of the breaking member 400 are influenced by the end portion such that the second contact portion 403 and the third contact portion 404 are unlikely to be deformed and are unlikely to approach the outer surface of the shaft 20. Therefore, when the breaking member 400 is stretched in the axial direction, thereby, being contracted in the radial direction, the second contact portion 403 and the third contact portion 404 remain curved and thus the second contact portion 403 and the third contact portion do not necessarily approach the shaft 20. Therefore, the second contact portion 403 and the third contact portion 404 are located more outward in the radial direction than the first contact portion 402.

The first contact portion 402, the second contact portion 403, and the third contact portion 404 curve in different directions from each other in the three dimensional view and have different curvature radius from each other. Therefore, the first contact portion 402, the second contact portion 403, and the third contact portion 404 can have different actions from each other with respect to the contact target. Incidentally, the second contact portion 403 and the third contact portion 404 may have the same curvature radius as each other. In the contracted state, when viewed from the distal side, the first convex portion 405A located in the second contact portion 403 is larger than the outer diameter of the first contact portion 402, and thereby the second contact portion 403 comes into strong contact with the thrombus B or the lumen tissue. In accordance with an exemplary embodiment, the second contact portion 403 curves in a three-dimensional manner, and thus the shape of the second contact portion changes depending on a direction of view. In the contracted state, when viewed from the front surface, the second contact portion 403 is observed as a steep projecting portion having a small width so as to overlap the wire 401 in the axial direction. In addition, in the contracted state, when viewed from side, the second contact portion 403 is observed as a gentle projecting portion having a larger width, compared with the case of being viewed from the front surface (refer to FIG. 20B). In addition, in the contracted state, when viewed from the distal side, the third convex portion 405C located in the third contact portion 404 is larger than the outer diameter of the first contact portion 402, and thereby the third contact portion 404 comes into strong contact with the thrombus B or the lumen tissue. In accordance with an exemplary embodiment, the third contact portion 404 curves in a three-dimensional manner, and thus the shape of the third contact portion changes depending on a direction of view. In the contracted state, when viewed from the front surface, the third contact portion 404 is observed as a steep projecting portion having a relatively smaller width so as to overlap the wire 401 in the axial direction. In addition, in the contracted state, when viewed from side, the third contact portion 404 is observed as a gentle projecting portion having a larger width, compared with the case of being viewed from the front surface (refer to FIG. 20B). In the expanded state, the first contact portion 402 is formed to have a shape approximate to a straight line so as to come into smooth contact with the thrombus B or the lumen tissue.

In the three dimensional view, the second contact portion 403 and the third contact portion 404 have the curvature radius smaller than that of the first contact portion 402, and thus the second contact portion 403 has a structure in which the second contact portion 403 is more difficult to be deformed against an applied force than the first contact portion 402. In accordance with an exemplary embodiment, the end portion of the breaking member 400 is fixed to the sliding portion 50 or the fixing portion 51 such that it is not possible to change a position and an orientation of the end portion, and thereby the second contact portion 403 and the third contact portion 404 that are closer to the end portion than the first contact portion 402 are influenced by the end portion such that the second contact portion 403 and the third contact portion 404 are unlikely to be deformed and are unlikely to approach the outer surface of the shaft 20. Hence, the second contact portion 403 and the third contact portion 404 have a more rigid structure than that of the first contact portion 402 and have a relatively high breaking force and agitating force. In accordance with an exemplary embodiment, in the three dimensional view, the first contact portion 402, the second contact portion 403, and the third contact portion 404 have the same curvature radius as each other; however, it is possible to have different actions from each other with respect to the contact target, for example, thrombus B.

In accordance with an exemplary embodiment, in the contracted state, the second contact portion 403 and the third contact portion 404 have the radially outward convex shape when viewed from the front surface, and the convex shape curves. Therefore, the second contact portion 403 and the third contact portion 404 easily break (i.e., enter) into the thrombus B in the body lumen in the contracted state. In addition, in the contracted state, the second contact portion 403 and the third contact portion 404 have the convex shape toward the circumferential direction (rotating direction) of the breaking member 400, and the convex shape curves. Therefore, the second contact portion 403 and the third contact portion 404 rotate, thereby, rather easily and strongly breaking into the thrombus B in the body lumen.

In a case where a large amount of the thrombus B which is the breaking target is present and the patency rate is low, the breaking member 400 in the medical device according to the fourth embodiment will be contracted so that the second contact portion 403 and the third contact portion 404, which are more rigid than the first contact portion 402, are located outward to come into contact with the thrombus B, which makes it possible to break the thrombus B rather efficiently. In a case where a small amount of the thrombus B which is the breaking target is present and the patency rate is relatively high, the breaking member 400 comes into the expanded state so that the first contact portion 402 is located most outward, which makes it possible to reduce the burden on the blood vessel caused by the rotation of the breaking member 400. The second contact portion 403 is located on the proximal side of the first contact portion 402, and the third contact portion 404 is located on the distal side of the first contact portion 402. Therefore, in the medical device according to the fourth embodiment, it is not only possible to break the thrombus B by the second contact portion 403 when the breaking member 400 is moved toward the proximal side, but also it is possible to break the thrombus B by the third contact portion 404 when the breaking member 400 is moved toward the distal side. Therefore, relatively high performance of breaking and agitating can be achieved.

Fifth Embodiment

A medical device according to a fifth embodiment differs from the medical device 10 according to the first embodiment only in that a breaking member 500 is provided. Incidentally, the same reference signs are assigned to parts having the same functions as those of the first embodiment, and thus the description of those same reference signs and same functions is omitted.

Figure 22:
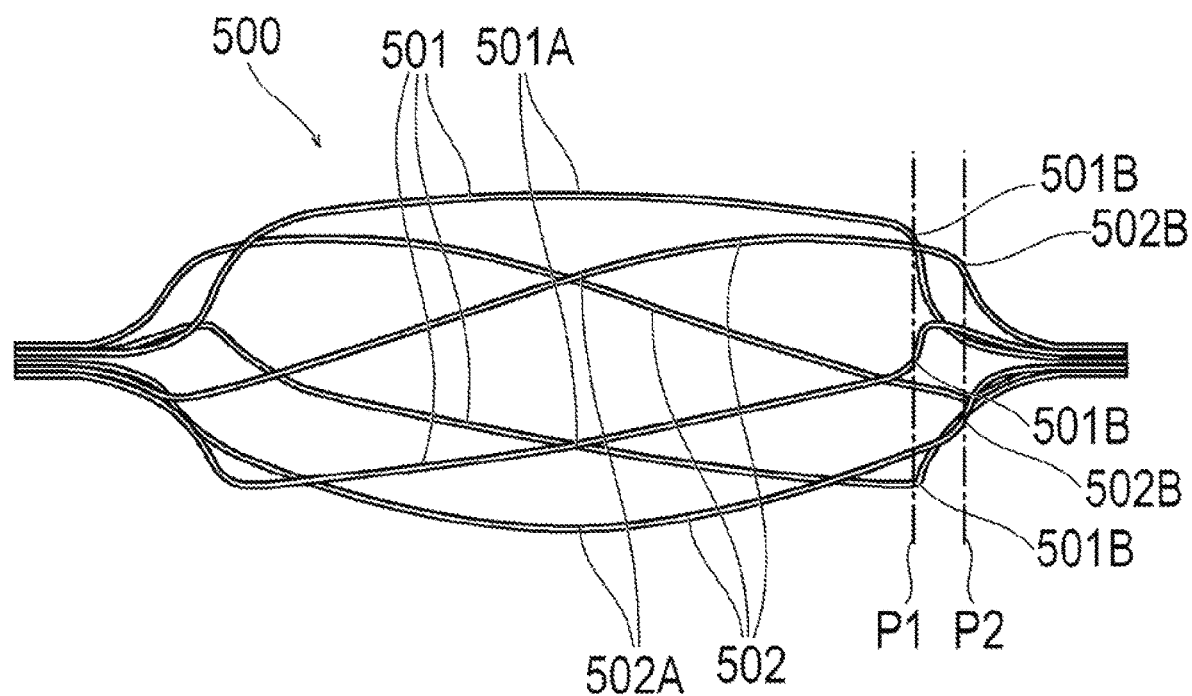
FIG. 22 is a side view illustrating a breaking member in an expanded state of a medical device according to a fifth embodiment.

As illustrated in FIG. 22, the breaking member 500 has a first wire 501 and a second wire 502 which are different from each other. The first wire 501 and the second wire 502 are disposed alternately in the circumferential direction. In accordance with an exemplary embodiment, the number of the first wires 501 and the second wires 502 is not particularly limited. The first wire 501 has a first contact portion 501A and a second contact portion 501B. In the expanded state in which the breaking member 500 is expanded radially outward, the first contact portion 501A is located most outward in the radial direction. In the expanded state, the first contact portion 501A is located more radially outward from the second contact portion 501B. In the contracted state in which the breaking member 500 is more contracted radially inward from the expanded state, the second contact portion 501B may be located more outward in the radial direction than the first contact portion 501A.

The second wire 502 has a first contact portion 502A and a second contact portion 502B. In the expanded state in which the breaking member 500 is expanded radially outward, the first contact portion 502A is located most outward in the radial direction. In accordance with an exemplary embodiment, a length of the first contact portion 502A in the radial direction is equal to a length of the first contact portion 501A of the first wire 501 in the radial direction. In accordance with an exemplary embodiment, the length of the first contact portion 501A in the radial direction may be different from the length of the first contact portion 502A in the radial direction. In the expanded state, the first contact portion 502A is located more radially outward than the second contact portion 502B. In the contracted state in which the breaking member 500 is more contracted radially inward from the expanded state, the second contact portion 502B may be located more outward in the radial direction than the first contact portion 502A. In the expanded state and the contracted state, the position P2 of the second contact portion 502B in the axial direction is located more proximal than the position P1 of the second contact portion 501B of the first wire 501 in the axial direction.

The medical device according to the fifth embodiment includes the first wire 501 and the second wire 502 which are different from each other, and the position P1 of the second contact portion 501B of the first wire 501 in the axial direction is different from the position P2 of the second contact portion 502B of the second wire 502 in the axial direction. Therefore, the medical device is capable of breaking and agitating an object such as thrombus at different positions P1 and P2 in the axial direction, and relatively high breaking force and agitating force are obtained.

Sixth Embodiment

A medical device according to a sixth embodiment differs from the medical device 10 according to the first embodiment only in that a breaking member 600 is provided. Incidentally, the same reference signs are assigned to parts having the same functions as those of the first embodiment, and thus the description of those same reference signs and same functions is omitted.

Figure 23:
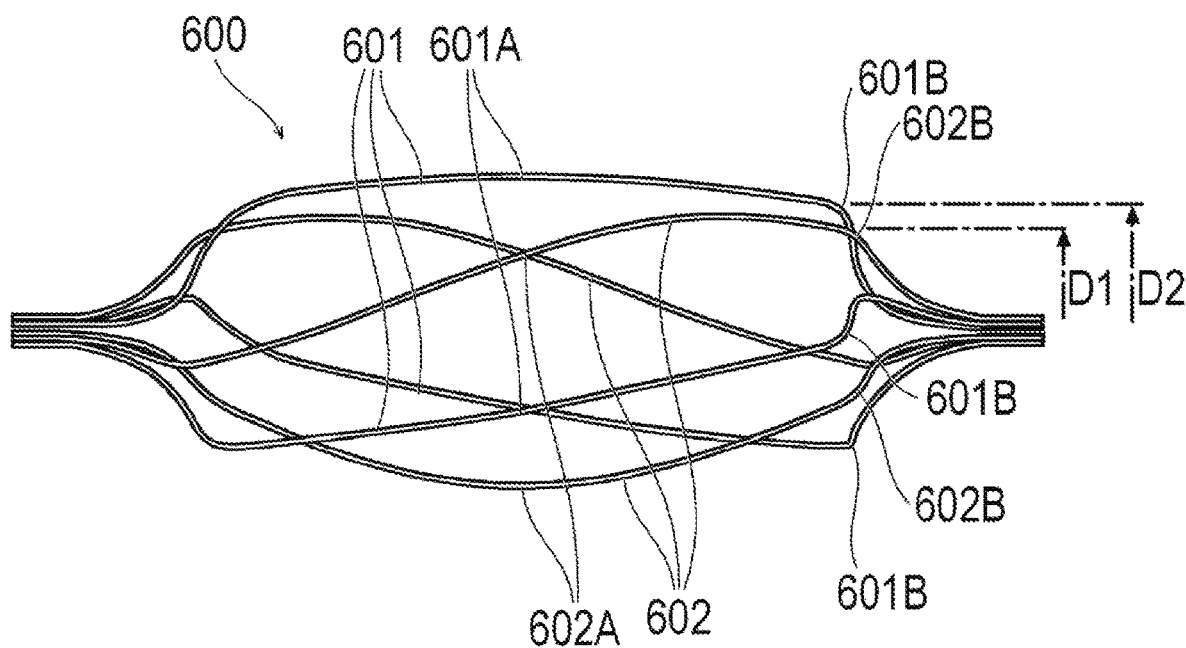
FIG. 23 is a side view illustrating a breaking member in an expanded state of a medical device according to a sixth embodiment.

As illustrated in FIG. 23, the breaking member 600 has a first wire 601 and a second wire 602 which are different from each other. The first wire 601 and the second wire 602 are disposed alternately in the circumferential direction. Incidentally, the number of the first wires 601 and the second wires 602 is not particularly limited. The first wire 601 has a first contact portion 601A and a second contact portion 601B. In the expanded state in which the breaking member 600 is expanded radially outward, the first contact portion 601A is located most outward in the radial direction. In the expanded state, the first contact portion 601A is located more radially outward than the second contact portion 601B. In the contracted state in which the breaking member 600 is contracted radially inward, rather than the expanded state, the second contact portion 601B can be located more outward in the radial direction than the first contact portion 601A.

The second wire 602 has a first contact portion 602A and a second contact portion 602B. In the expanded state in which the breaking member 600 is expanded radially outward, the first contact portion 602A is located most outward in the radial direction. In accordance with an exemplary embodiment, a length of the first contact portion 602A in the radial direction is equal to a length of the first contact portion 601A of the first wire 601 in the radial direction. In accordance with an exemplary embodiment, the length of the first contact portion 601A in the radial direction may be different from the length of the first contact portion 602A in the radial direction. In the expanded state, the first contact portion 602A is located more radially outward than the second contact portion 602B. In the contracted state in which the breaking member 600 is more contracted radially inward from the expanded state, the second contact portion 602B can be located more outward in the radial direction than the first contact portion 602A. In the expanded state, a length D1 of the second contact portion 601B of the first wire 601 in the radial direction is larger than a length D2 of the second contact portion 602B in the radial direction. In the contracted state, the first wire 601 and the second wire 602 are contracted in the radial direction overall. Therefore, a difference between D1 and D2 in the contracted state is smaller than a difference between D1 and D2 in the expanded state. A position of the second contact portion 601B in the axial direction is substantially coincident with a position of the second contact portion 602B in the axial direction; however, the positions may not be coincident with each other.

The medical device according to the sixth embodiment includes the first wire 601 and the second wire 602 which are different from each other, and the length D1 of the second contact portion 601B of the first wire 601 in the radial direction is different from the length D2 of the second contact portion 602B of the second wire 602 in the radial direction. The difference between D1 and D2 increases as the breaking member 600 is expanded. Therefore, as the breaking member 600 is expanded, the second contact portion 602B having a short length in the radial direction is unlikely to come into contact with the blood vessel. Hence, safety of the medical device can be improved.

Seventh Embodiment

A medical device according to a seventh embodiment differs from the medical device 10 according to the first embodiment only in that a breaking member 700 is provided. Incidentally, the same reference signs are assigned to parts having the same functions as those of the first embodiment, and thus the description of the same reference signs and same functions is omitted.

Figure 24:
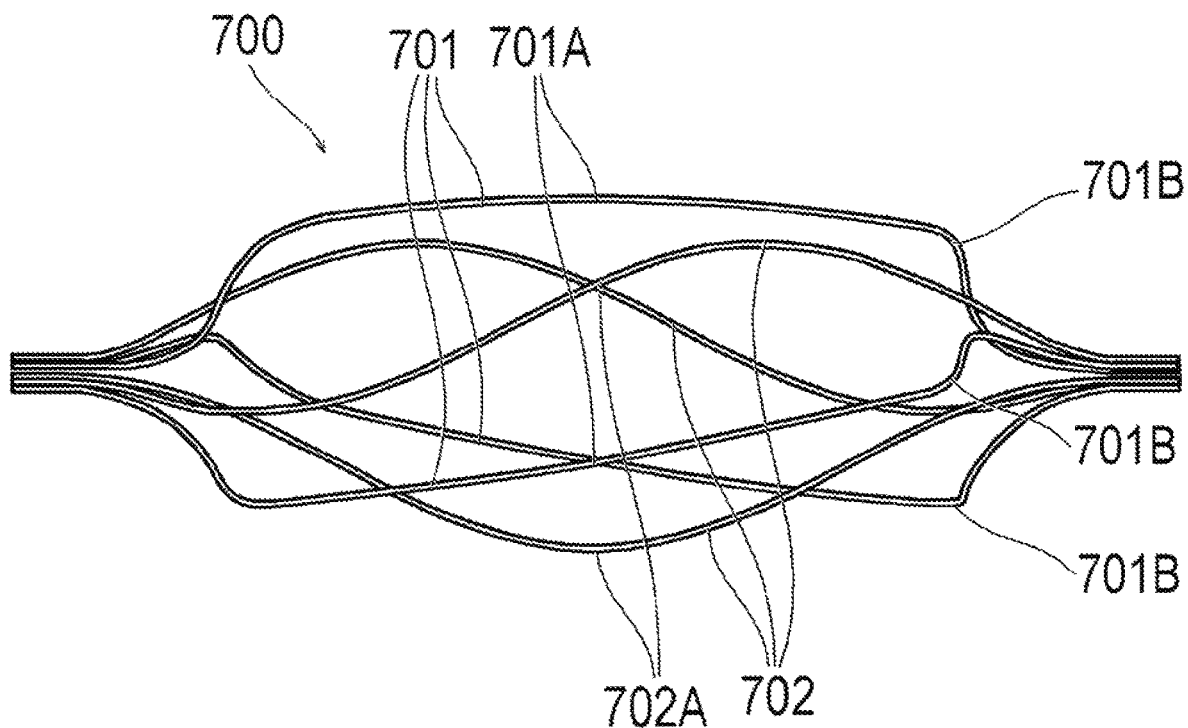
FIG. 24 is a side view illustrating a breaking member in an expanded state of a medical device according to a seventh embodiment.

As illustrated in FIG. 24, the breaking member 700 has a first wire 701 and a second wire 702 which are different from each other. The first wire 701 and the second wire 702 are disposed alternately in the circumferential direction. Incidentally, the number of the first wires 701 and the second wires 702 is not particularly limited. The first wire 701 has a first contact portion 701A and a second contact portion 701B. In the expanded state in which the breaking member 700 is expanded radially outward, the first contact portion 701A is located most outward in the radial direction. In the expanded state, the first contact portion 701A is located more radially outward than the second contact portion 701B. In the contracted state in which the breaking member 700 is more contracted radially inward, rather than the expanded state, the second contact portion 701B can be located more outward in the radial direction than the first contact portion 701A.

The second wire 702 has a first contact portion 702A. In the expanded state in which the breaking member 700 is expanded radially outward, the first contact portion 702A is located most outward in the radial direction. In other words, the length of the first contact portion 702A in the radial direction is equal to the length of the first contact portion 701A of the first wire 701 in the radial direction. Incidentally, the length of the first contact portion 701A in the radial direction may be different from the length of the first contact portion 702A in the radial direction. In the contracted state in which the breaking member 700 is contracted radially inward, rather than the expanded state, the second wire 702 is not provided with a second contact portion that is to be located more outward in the radial direction than the first contact portion 702A.

The medical device according to the seventh embodiment includes the first wire 701 and the second wire 702 which are different from each other, and only the first wire 701 has the second contact portion 701B that is located more outward in the radial direction than the first contact portion 702A in the contracted state. Therefore, it is possible to appropriately set the number of the second contact portions 701B, which are provided, in the breaking member 700. Hence, it is possible to set the breaking force of the breaking member 700 to a desirable value.

In accordance with an exemplary embodiment, the disclosure is not limited only to the embodiments described above, and it is possible for those skilled in the art to perform various modifications within the technical ideas of the disclosure. In addition, the body lumen, into which the medical device is inserted, is not limited to the blood vessel, and examples of the body lumen may include a vessel, a ureter, a bile duct, an oviduct, a hepatic duct, or the like. Hence, the object to be broken may not be the thrombus.

In addition, in the embodiment described above, the second contact portion is located on the proximal side of the first contact portion; however, the first contact portion may be located on the distal side of the second contact portion. In addition, the second contact portion may be provided on both the distal side and the proximal side of the first contact portion. In addition, a plurality of second contact portions may be arranged on one wire.

In addition, the wire that configures the breaking member may have the connection portion on the distal side and the connection portion on the proximal side, in which the wire is connected to the shaft, at the same position as each other in the circumferential direction. Hence, the wire that configures the breaking member may not have the spiral shape or may have a straight line shape in the axial direction in the developed view in the circumferential direction.

In addition, as a method of forming the first soft contact portion and the second hard contact portion, a wire diameter of the wire may be decreased in the first soft contact portion, and the wire diameter of the wire may be increased in the second hard contact portion. The wire provided with the first contact portion and the wire provided with the second contact portion may be the same wire or may be different from each other.

In addition, the wire in the first soft contact portion may be made of a soft material, and the wire in the second hard contact portion may be made of a harder material than the first contact portion. The wire provided with the first contact portion and the wire provided with the second contact portion may be the same wire or may be different from each other.

In addition, the wire provided with the first soft contact portion may be a single wire, and the wire provided with the second hard contact portion may be made of stranded wire. In addition, a part of the wire may be coated, and the part may be set as the second hard contact portion.

In addition, a part of the wire may be broken (changing a sectional shape) so as to be easily bent, and the part may be set as the first contact portion. In addition, a part of the wire may be broken (changing a sectional shape) such that it is difficult to bend the wire, and the part may be set as the second contact portion. In addition, a movable portion (for example, a universal joint) may be provided in the wire so as to be easily bent, and thereby the first contact portion may be provided.

In addition, a part of the wire may be quenched or annealed, and thereby the first hard contact portion or the second soft contact portion may be provided. In addition, a corrugated process (spiral cutting) may be performed on a part of the wire so as to provide the first soft contact portion.

In addition, the wire may be a tube body, spiral cutting may be performed on the tube body, and thereby the first contact portion that is soft may be obtained. In addition, the wire may be a tube body, a core bar may be provided in a part of the tube body, and thereby the second hard contact portion may be provided.

In addition, in a case where the wire provided with the first contact portion and the wire provided with the second contact portion are different from each other, the number of wires may be different from each other. For example, the wires provided with the second contact portion are increased, and thereby it is possible to increase the breaking force and the agitating force.

In addition, in the first embodiment, the proximal portion of the breaking member 60 is fixed to the sliding portion 50 that is slidable with respect to the shaft 20; however, the distal portion of the breaking member may be fixed to the sliding portion.

The detailed description above describes a medical device and a treatment method using the medical device that is used for breaking an object in a body lumen. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device configured to be inserted into a body lumen to break an object in the body lumen, the medical device comprising:
an elongated shaft configured to be rotatably driven;
a deformable breaking member that is connected to the shaft and configured to be rotatable and extends along the shaft, the breaking member having a first contact portion and a second contact portion, the first contact portion being located more outward in a radial direction of the breaking member than the second contact portion in a state in which the breaking member is expanded radially outward, and wherein the second contact portion is located more outward in the radial direction of the breaking member than the first contact portion in a contracted state;
the breaking member comprising a plurality of wires, and wherein proximal-side end portions of the plurality of wires are each fixed to a sliding member configured to be slidable with respect to and movable along the elongated shaft and distal-side end portions of the plurality of wires are each fixed to a fixing member is fixed to the elongated shaft; and
one or more of the plurality of wires having a convex portion in a developed view in a circumferential direction in the expanded state.

2. The medical device according to claim 1, wherein the first contact portion is located more outward in the radial direction of the breaking member than the second contact portion in a natural state in which the breaking member is expanded radially outward with no external force acting on the breaking member.

3. The medical device according to claim 1, wherein the second contact portion is more rigid than the first contact portion.

4. The medical device according to claim 1, wherein the first contact portion has a shape different from that of the second contact portion.

5. The medical device according to claim 1, wherein the first contact portion is located to be closer to a center portion of the breaking member in an axial direction of the breaking member than the second contact portion in the expanded state.

6. The medical device according to claim 1, wherein the second contact portion curves to have a curvature radius smaller than that of the first contact portion in the expanded state.

7. The medical device according to claim 1, wherein the second contact portion curves to have a radially outward convex shape in the contracted state.

8. The medical device according to claim 1, wherein the second contact portion curves to have a convex shape toward a rotating direction in the contracted state.

9. The medical device according to claim 1, wherein positions of a connection portion on a distal side and a connection portion on a proximal side, in which a wire of the plurality of wires is connected to the shaft, are different from each other in a circumferential direction.

10. The medical device according to claim 1, further comprising:
    each of the plurality of wires having an inflection point between the first contact portion and the second contact portion in the expanded state.

11. The medical device according to claim 1, wherein the plurality of wires are made from a shape-memory alloy.

12. The medical device according to claim 10, wherein each of the plurality of the wires has a first convex portion, a second convex portion, and a third convex portion; and
    wherein the first convex portion, the second convex portion, and the third convex portion have equal curvature radius in a circumferential direction, and wherein the first convex portion and the third convex portion project on a same side in the circumferential direction.

13. The medical device according to claim 1, wherein the first contact portion has a third contact portion having a curve shape and a fourth contact portion having a straight line shape in a circumferential direction.

14. The medical device according to claim 1, wherein the one or more of the plurality of wires has a straight portion in the developed view in the circumferential direction in the expanded state.

15. The medical device according to claim 1, wherein the convex portion of the one or more of the plurality of wires is positioned on a distal side of the breaking member.

16. The medical device according to claim 15, wherein the convex portion of the one or more of the plurality of wires projects in the radial direction of the breaking member.

17. A treatment method for breaking an object in a body lumen by using the medical device according to claim 1, the treatment method comprising:
    inserting the shaft into the body lumen and delivering the breaking member to a vicinity of the object; and
    inserting the breaking member into a gap of the object and rotating the breaking member by the shaft to break the object while deforming the breaking member due to an elastic force of the breaking member depending on a size of the gap of the object to change a contact position with the object to the first contact portion or the second contact portion in a radial direction.

18. A medical device configured to be inserted into a body lumen to break an object in the body lumen, the medical device comprising:
    an elongated shaft configured to be rotatably driven;
    deformable breaking members that are connected to the elongated shaft and configured to be rotatable, the deformable members extending along the shaft and arranged along a circumferential direction, wherein the breaking members have a first contact portion and a second contact portion, the second contact portion being more rigid than the first contact portion, the first contact portion being located more outward in a radial direction of the breaking member than the second contact portion in a state in which the breaking member is expanded radially outward, and wherein the second contact portion is located more outward in the radial direction of the breaking member than the first contact portion in a contracted state;
    the breaking member comprising a plurality of wires, and wherein proximal-side end portions of the plurality of wires are each fixed to a sliding member configured to be slidable with respect to and movable along the elongated shaft and distal-side end portions of the plurality of wires are each fixed to a fixing member that is fixed to the elongated shaft; and
    wherein in a developed view in the circumferential direction in the expanded state, one or more of the plurality of wires having a convex portion on a proximal side of the one or more of the plurality of wires in a range that excludes a fixing range for fixing the plurality of wires to the sliding member or the fixing member of the medical device.

19. The medical device according to claim 18, wherein the first contact portion is located more outward in a radial direction of the breaking members than the second contact portion in a state in which the breaking members are expanded radially outward, and wherein the second contact portion is located more outward in the radial direction of the breaking members than the first contact portion in a contracted state.

20. The medical device according to claim 18, wherein the first contact portion is located more outward in the radial direction of the breaking members than the second contact portion in a natural state in which the breaking members are expanded radially outward with no external force acting on the breaking members.

21. A medical device configured to be inserted into a body lumen to break an object in the body lumen, the medical device comprising:
    an elongated shaft configured to be rotatably driven;
    a deformable breaking member having a plurality of wires, and wherein proximal-side end portions of the plurality of wires are each fixed to a sliding member configured to be slidable with respect to and movable along the elongated shaft and distal-side end portions of the plurality of wires are each fixed to a fixing member that is fixed to the elongated shaft the breaking member having a first contact portion and a second contact portion, the first contact portion being located more outward in a radial direction of the breaking member than the second contact portion in a state in which the breaking member is expanded radially outward, and wherein the second contact portion is located more outward in the radial direction of the breaking member than the first contact portion in a contracted state; and wherein in a developed view in the circumferential direction in the expanded state, each of the plurality of wires having a convex portion in a range that excludes a fixing range for fixing the plurality of wires to the sliding member or the fixing member of the medical device.

22. The medical device according to claim 21, wherein the second contact portion is located distal to the first contact portion.

23. The medical device according to claim 21, wherein the convex portion of each of the plurality of wires is positioned on a distal side of the breaking member.

24. The medical device according to claim 23, wherein the convex portion of each of the plurality of wires projects in a radial direction of the breaking member.

* * * * *